(12) United States Patent
Busch-Petersen

(10) Patent No.: US 8,097,626 B2
(45) Date of Patent: Jan. 17, 2012

(54) IL-8 RECEPTOR ANTAGONISTS

(75) Inventor: Jakob Busch-Petersen, King of Prussia, PA (US)

(73) Assignee: GlaxoSmithKline LLC, Philadelphia, PA (US)

( * ) Notice: Subject to any disclaimer, the term of this patent is extended or adjusted under 35 U.S.C. 154(b) by 146 days.

(21) Appl. No.: 12/297,917

(22) PCT Filed: Apr. 20, 2007

(86) PCT No.: PCT/US2007/067088
§ 371 (c)(1),
(2), (4) Date: Jul. 29, 2009

(87) PCT Pub. No.: WO2007/124423
PCT Pub. Date: Nov. 1, 2007

(65) Prior Publication Data
US 2009/0298810 A1 Dec. 3, 2009

Related U.S. Application Data

(60) Provisional application No. 60/793,836, filed on Apr. 21, 2006.

(51) Int. Cl.
*A01N 43/58* (2006.01)
*A61K 31/50* (2006.01)

(52) U.S. Cl. .................................. 514/247; 544/336
(58) Field of Classification Search .................. 544/336; 514/247
See application file for complete search history.

(56) References Cited

U.S. PATENT DOCUMENTS

| | | |
|---|---|---|
| 1,792,156 A | 2/1931 | Fitzky |
| 2,363,074 A | 11/1944 | Martin et al. |
| 2,407,309 A | 9/1946 | Lott et al. |
| 2,795,610 A | 6/1957 | Gerjovich |
| 3,647,819 A | 3/1972 | Kirchner |
| 3,689,550 A | 9/1972 | Schellenbaum et al. |
| 3,932,434 A | 1/1976 | Paget et al. |
| 3,966,968 A | 6/1976 | Andree et al. |
| 3,996,253 A | 12/1976 | Magagnoli et al. |
| 4,008,326 A | 2/1977 | Callahan et al. |
| 4,048,333 A | 9/1977 | Galabov et al. |
| 4,405,644 A | 9/1983 | Kabbe et al. |
| 4,591,604 A | 5/1986 | Conrow et al. |
| 4,608,205 A | 8/1986 | Conrow et al. |
| 5,206,234 A | 4/1993 | Bock et al. |
| 5,215,570 A | 6/1993 | Burckhardt et al. |
| 5,262,415 A | 11/1993 | Takemoto et al. |
| 5,290,814 A | 3/1994 | Jackson et al. |
| 5,312,831 A | 5/1994 | Ayral-Kaloustian et al. |
| 5,401,758 A | 3/1995 | Atwal et al. |
| 5,441,984 A | 8/1995 | Heath, Jr. et al. |
| 5,464,863 A | 11/1995 | Nagamine et al. |
| 5,576,335 A | 11/1996 | Sueda et al. |
| 5,585,518 A | 12/1996 | Marschner et al. |
| 5,621,010 A | 4/1997 | Sueda et al. |
| 5,696,138 A | 12/1997 | Olesen et al. |
| 5,780,483 A | 7/1998 | Widdowson et al. .......... 514/311 |
| 5,886,044 A | 3/1999 | Widdowson et al. .......... 514/596 |
| 5,929,250 A | 7/1999 | Widdowson et al. ...... 548/361.1 |
| 6,005,008 A | 12/1999 | Widdowson et al. .......... 514/596 |
| 6,133,319 A | 10/2000 | Widdowson et al. .......... 514/598 |
| 6,177,448 B1 | 1/2001 | Widdowson et al. .......... 514/319 |
| 6,180,675 B1 | 1/2001 | Widdowson et al. .......... 514/586 |
| 6,204,294 B1 | 3/2001 | Bryan et al. .................. 514/609 |
| 6,211,373 B1 | 4/2001 | Widdowson et al. .......... 546/146 |
| 6,214,880 B1 | 4/2001 | Houze |
| 6,214,881 B1 | 4/2001 | Xiang |
| 6,218,539 B1 | 4/2001 | Widdowson et al. ............. 546/1 |
| 6,221,889 B1 | 4/2001 | Rutledge, Jr. et al. ........ 514/373 |
| 6,248,785 B1 | 6/2001 | Widdowson et al. .......... 514/603 |
| 6,262,113 B1 | 7/2001 | Widdowson et al. .......... 514/522 |
| 6,271,261 B1 | 8/2001 | Widdowson et al. .......... 514/585 |
| 6,297,265 B2 | 10/2001 | Widdowson et al. .......... 514/367 |
| 6,300,325 B1 | 10/2001 | Widdowson et al. .......... 514/111 |
| 6,316,478 B1 | 11/2001 | Widdowson et al. .......... 514/373 |
| 6,335,352 B1 | 1/2002 | Bryan et al. .................. 514/365 |
| 6,372,933 B1 | 4/2002 | Baine et al. |
| 6,436,927 B1 | 8/2002 | Nie et al. .................... 514/222.8 |
| 6,440,993 B1 | 8/2002 | Widdowson .................... 514/30 |
| 6,500,863 B1 | 12/2002 | Jin et al. .................... 514/227.5 |
| 6,566,387 B1 | 5/2003 | Palovich et al. ............... 514/398 |
| 6,608,077 B2 | 8/2003 | Widdowson et al. ........... 564/79 |
| 6,653,310 B2 | 11/2003 | Palovich et al. ............... 514/247 |
| 6,653,347 B2 | 11/2003 | Palovich et al. ................ 514/24 |
| 6,664,259 B2 | 12/2003 | Widdowson et al. ............. 514/2 |
| 6,680,317 B2 | 1/2004 | Palovich et al. .......... 514/252.12 |
| 6,767,922 B2 | 7/2004 | Widdowson et al. .......... 514/522 |
| 7,008,962 B2 | 3/2006 | Palovich et al. ............... 514/524 |
| 2001/0047002 A1 | 11/2001 | Sit et al. |
| 2003/0028042 A1 | 2/2003 | Palovich et al. ............... 558/199 |
| 2003/0032802 A1 | 2/2003 | Palovich et al. ............... 540/609 |
| 2003/0050298 A1 | 3/2003 | Palovich et al. .......... 514/210.01 |
| 2003/0065170 A1 | 4/2003 | Widdowson et al. .......... 540/544 |
| 2003/0097004 A1 | 5/2003 | Taveras et al. |
| 2003/0100608 A1 | 5/2003 | Cirillo et al. |
| 2003/0109527 A1 | 6/2003 | Jin et al. |
| 2003/0204085 A1 | 10/2003 | Taveras et al. |
| 2003/0225125 A1 | 12/2003 | Widdowson et al. |
| 2004/0038854 A1 | 2/2004 | Dillon et al. ..................... 514/1 |
| 2004/0048897 A1 | 3/2004 | McCleland et al. ........... 514/338 |
| 2004/0110954 A1 | 6/2004 | Palovich et al. |
| 2004/0132694 A1 | 7/2004 | Palovich et al. |

(Continued)

FOREIGN PATENT DOCUMENTS

AU 93134950 3/1993

(Continued)

OTHER PUBLICATIONS

U.S. Appl. No. 12/297,885, filed Oct. 21, 2008, Busch-Petersen.

(Continued)

*Primary Examiner* — Paul V. Ward
(74) *Attorney, Agent, or Firm* — Robert H. Brink

(57) ABSTRACT

This invention relates to novel compounds and compositions thereof, useful in the treatment of disease states mediated by the chemokine, Interleukin-8 (Il-8).

9 Claims, No Drawings

U.S. PATENT DOCUMENTS

| | | | |
|---|---|---|---|
| 2006/0040952 A1 | 2/2006 | Busch-Petersen et al. | 514/255.02 |
| 2006/0084641 A1 | 4/2006 | McCleland et al. | 514/218 |
| 2006/0122173 A1 | 6/2006 | Busch-Petersen et al. | |
| 2007/0249625 A1 | 10/2007 | Busch-Petersen et al. | |
| 2007/0249672 A1 | 10/2007 | Busch-Petersen | |
| 2009/0093451 A1 | 4/2009 | Busch-Peterson | |
| 2009/0170871 A1 | 7/2009 | Busch-Peterson et al. | |

FOREIGN PATENT DOCUMENTS

| | | |
|---|---|---|
| CH | 506240 | 6/1971 |
| EP | 0344425 B1 | 12/1989 |
| EP | 0656350 A | 9/1994 |
| FR | 2100943 | 7/1972 |
| GB | 1011940 | 12/1965 |
| GB | 1 210 596 | 10/1970 |
| GB | 2079480 | 1/1982 |
| JP | 55098152 A | 7/1980 |
| WO | 97/49287 | 12/1997 |
| WO | 97/49399 | 12/1997 |
| WO | 98/06701 | 1/1998 |
| WO | 98/05328 | 2/1998 |
| WO | 98/06262 | 2/1998 |
| WO | 98/06398 | 2/1998 |
| WO | 99/06354 | 1/1999 |
| WO | 99/36069 | 7/1999 |
| WO | 00/06557 | 2/2000 |
| WO | 00/12468 | 3/2000 |
| WO | 00/12461 | 9/2000 |
| WO | 00/69435 | 11/2000 |
| WO | 00/72800 | 12/2000 |
| WO | 00/72840 | 12/2000 |
| WO | 00/73282 | 12/2000 |
| WO | 00/76457 | 12/2000 |
| WO | 00/76495 | 12/2000 |
| WO | 00/76501 | 12/2000 |
| WO | 00/76508 | 12/2000 |
| WO | 00/76516 | 12/2000 |
| WO | 00/76517 | 12/2000 |
| WO | 01/07045 | 2/2001 |
| WO | 01/34141 | 5/2001 |
| WO | 2007/124423 | 11/2007 |
| WO | 2007/150015 | 12/2007 |
| WO | 2007150016 | 12/2007 |
| WO | 2008/070707 | 6/2008 |

OTHER PUBLICATIONS

Broome et al., Ind Chem Belge, vol. 32, pp. 204-208, 1967.
Baggiolini et al., FEBS Lett. 307, 97 (1992).
Craig et al., Drug metabolism and Disposition, Vo. 17 (3), pp. 345-347 (1989).
Davidkov, Chemical Abstracts, 110, 5, #32929n (1989), XP-002173840.
Donnelly et al., Lancet, vol. 341, No. 8846, Mar. 1993.
Gruenke, Larry D. et al., J. Anal. Toxicol., 11(2), pp. 75-80 (1987).
Hauptmann et al., Chemical Abstracts, vol. 109, No. 25, 1988, p. 816. Abstract No. 230,571k.
Hay, et al. Current Opinion in Pharmacology, 2001, 1:242-247.
Hiles, Richard A. et al., Toxicol. Appl. Pharmacol., 46 (2), 323-37 (1978).
Jeffcoat, A. Robert et al., Drug Metab. Dispos., 5 (2), 157-66 (1980).
Kalcheva, et al., Caplus 1989:38704, 110:38704.
Khurana, et al., Chemical Era, vol. 14(9) pp. 383-386 1978.
Koch et al., Science 258, 1798 (1992).
Li, Jie Jack, Expert Opin. Ther. Patents, vol. 11 (12), 2001.
Lozanova et al., Dokl. Bulg. Akad. Nauk, 46(11), pp. 85-88 (1993).
Olesen et al., Chemical Abstracts, 122(7) (1995), pp. 1042-43 CA 122: :80891s.
Patil et al., Indian J. Pharm. Sci., vol. 49 (6), 229-231 (1987).
Pavia, J Med Chem vol. 33, pp. 854-861 1990.
Ponath, et al., Expert Opinion on Investigational Drugs, vol. 7, No. 1 (1998).
Tanaka, Fred S. et al., J. Agric. Food Chem., 27 (2), 311-15 (1979)., XP002173842.
Teran et al., Am J Resp Crit Care Med, vol. 155(4) pp. 1362-1366 1997.
Davidkov, K., Chemistry of Heterocyclic Compounds, 17, 2, 124-125 (1981).
Hadjieva et al., Comptes Rendus de LAcademie Bulgaria des Sciences, vol. 41, No. 11 (1988).
Franke, R. et al., Relationship between structure & cytotoxicity, Dokl. Bolg. Akad. Nauk, 32 (3), pp. 369-371 (1979).
Galabov, A. et al., Inhibitory effect of N-phenyl-N'aryl, Chemotherapy 17 (3), pp. 161-174 (1972).
Galabov, A.S., N-Phenyl-N'-aryl-or aklylthiourea derivatives, Prog. Chemother., 2, 981-5 (1973).
Galabov, Angel et al., Structure-activity relationship of diphenylthioure, J. Med. Chem., 23 (9), pp. 1048-51 (1980).
Karanov, Emanuil et al., Chem. structure and growth-regulating, Izv. Inst. Fiziol. Rast., Bulg. Akad. Nauk, 16, pp. 167-89 (1970).
Iwamura, Hajime, et al., Quantitative structure-activity relationship, Phytochemistry, 19 (7), 1309-19 (1980).
Krause, G. et al., Quantitative structure-activity relations, Biochem. Physiol. Pflanz., 174 (2), 128-38 (1979).
Lee et al., Immunol. Lett., 53, 109-113 (1996).
Schroder et al., J. Immunol. 139, 3474 (1987).
Vasilev, G. et al., Cytotoxic effect of certain derivatives of, Dokl. Bolg. Akad. Nauk, 22 (5), 567-70 (1969).
Vasilev, G.N. et al., Synthesis, chemical structure, and cytokinin-like, Biochem. Physiol, Pflanz., 165 (5/6), 467-78 (1974).
Widdowson et al., Discovery and Characterization of Potent Small Molecule Interleukin 8B Receptor Antagonists, Proceedings of the European Peptide Symposium, Sep. 8-13, 1996, Chemical Abstracts No. 1998:597604.
Interleukin-8 Receptor Antagonists, Expert Opinion on Therapeutic Patents, vol. 8, No. 4, pp. 471-473 (1998).
Chapman et al., Pharmacology & Therapeutics, 121, p. 55-68 (2009).
Sticherling et al., Arch Dermatol Rese 284, p. 82-85 (1992).
Kimata et al., Archives of Disease in Childhood, 70, p. 119-122 (1994).
Diag et al., Gut, 38, p. 216-222 (1996).
Baxter et al., Bioogranic & Medicinal Chemistry Letters, 13. p. 2625-2628 (2003).
White et al., J. Biol Chemistry, 273 (17) p. 10095-10098 (1998).
Nicholson et al., Pulmonary Pharmacology & Therapeutics, 20 p. 52-59 (2007).
Carpenter et al., European Respiratory Journal, 24, Suppl 48, p. 218 [P1382](2004).
U.S. Appl. No. 12/306,024, filed Oct. 21, 2008, Busch-Peterson et al.

IL-8 RECEPTOR ANTAGONISTS

This application is a 371 of International Application No. PCT/US2007/067088, filed 20 Apr. 2007, which claims the benefit of U.S. Provisional Application No. 60/793,836, filed 21 Apr. 2006, which are incorporated herein in their entirety.

FIELD OF THE INVENTION

This invention relates to novel sulfonamide substituted diphenyl urea compounds, pharmaceutical compositions, processes for their preparation, and use thereof in treating IL-8, GROα, GROβ, GROγ, NAP-2, and ENA-78 mediated diseases.

BACKGROUND OF THE INVENTION

Many different names have been applied to Interleukin-8 (IL-8), such as neutrophil attractant/activation protein-1 (NAP-1), monocyte derived neutrophil chemotactic factor (MDNCF), neutrophil activating factor (NAF), and T-cell lymphocyte chemotactic factor. Interleukin-8 is a chemoattractant for neutrophils, basophils, and a subset of T-cells. It is produced by a majority of nucleated cells including macrophages, fibroblasts, endothelial and epithelial cells exposed to TNF, IL-1α, IL-1β or LPS, and by neutrophils themselves when exposed to LPS or chemotactic factors such as FMLP. M. Baggiolini et al., *J. Clin. Invest.* 84, 1045 (1989); J. Schroder et al, *J. Immunol.* 139, 3474 (1987) and *J. Immunol.* 144, 2223 (1990); Strieter, et al., *Science* 243, 1467 (1989) and *J. Biol. Chem.* 264, 10621 (1989); Cassatella et al., *J. Immunol.* 148, 3216 (1992).

GROα, GROβ, GROγ and NAP-2 also belong to the chemokine family. Like IL-8 these chemokines have also been referred to by different names. For instance GROα, β, γ have been referred to as MGSAα, β and γ respectively (Melanoma Growth Stimulating Activity), see Richmond et al., *J. Cell Physiology* 129, 375 (1986) and Chang et al., *J. Immunol.* 148, 451 (1992). All of the chemokines of the α-family which possess the ELR motif directly preceding the CXC motif bind to the IL-8 B receptor (CXCR2).

IL-8, GROα, GROβ, GROγ, NAP-2, and ENA-78 stimulate a number of functions in vitro. They have all been shown to have chemoattractant properties for neutrophils, while IL-8 and GROα have demonstrated T-lymphocytes, and basophilic chemotactic activity. In addition IL-8 can induce histamine release from basophils from both normal and atopic individuals. GRO-α and IL-8 can in addition, induce lysozomal enzyme release and respiratory burst from neutrophils. IL-8 has also been shown to increase the surface expression of Mac-1 (CD11b/CD18) on neutrophils without de novo protein synthesis. This may contribute to increased adhesion of the neutrophils to vascular endothelial cells. Many known diseases are characterized by massive neutrophil infiltration. As IL-8, GROα, GROβ, GROγ and NAP-2 promote the accumulation and activation of neutrophils, these chemokines have been implicated in a wide range of acute and chronic inflammatory disorders including psoriasis and rheumatoid arthritis, Baggiolini et al., *FEBS Lett.* 307, 97 (1992); Miller et al., *Crit. Rev. Immunol.* 12, 17 (1992); Oppenheim et al., *Annu. Rev. Immunol.* 9, 617 (1991); Seitz et al., *J. Clin. Invest.* 87, 463 (1991); Miller et al., *Am. Rev. Respir. Dis.* 146, 427 (1992); Donnely et al., *Lancet* 341, 643 (1993). In addition the ELR chemokines (those containing the amino acids ELR motif just prior to the CXC motif) have also been implicated in angiostasis, Strieter et al., *Science* 258, 1798 (1992).

In vitro, IL-8, GROα, GROβ, GROγ and NAP-2 induce neutrophil shape change, chemotaxis, granule release, and respiratory burst, by binding to and activating receptors of the seven-transmembrane, G-protein-linked family, in particular by binding to IL-8 receptors, most notably the IL-8β receptor (CXCR2). Thomas et al., *J. Biol. Chem.* 266, 14839 (1991); and Holmes et al., *Science* 253, 1278 (1991). The development of non-peptide small molecule antagonists for members of this receptor family has precedent. For a review see R. Freidinger in: *Progress in Drug Research*, Vol. 40, pp. 33-98, Birkhauser Verlag, Basel 1993. Hence, the IL-8 receptor represents a promising target for the development of novel anti-inflammatory agents.

Two high affinity human IL-8 receptors (77% homology) have been characterized: IL-8Rα, which binds only IL-8 with high affinity, and IL-8β, which has high affinity for IL-8 as well as for GROα, GROβ, GROγ and NAP-2. See Holmes et al., supra; Murphy et al., *Science* 253, 1280 (1991); Lee et al., *J. Biol. Chem.* 267, 16283 (1992); LaRosa et al., *J. Biol. Chem.* 267, 25402 (1992); and Gayle et al., *J. Biol. Chem.* 268, 7283 (1993).

There remains a need for treatment, in this field, for compounds, which are capable of binding to the IL-8 α or β receptor. Therefore, conditions associated with an increase in IL-8 production (which is responsible for chemotaxis of neutrophil and T-cells subsets into the inflammatory site) would benefit by compounds, which are inhibitors of IL-8 receptor binding.

SUMMARY OF THE INVENTION

The present invention comprises novel IL-8 receptor antagonists represented by Formula (I), and compositions comprising the present compounds and a pharmaceutically acceptable carrier or diluent.

The present invention comprises novel IL-8 receptor antagonists represented by Formula (I), and combination comprising the present compounds and one or more additional therapeutic agents.

The present invention further comprises a method of treating a chemokine mediated disease wherein the chemokine is one which binds to an IL-8α or β receptor, and which method comprises administering an effective amount of a compound of Formula (I) or a pharmaceutically acceptable salt thereof.

The present invention also relates to a method of inhibiting the binding of IL-8 to its receptors in a mammal, particularly in a human, in need thereof which comprises administering an effective amount of a compound of Formula (I).

DETAILED DESCRIPTION OF THE INVENTION

Compounds of Formula (I) useful in the present invention are represented by the structure:

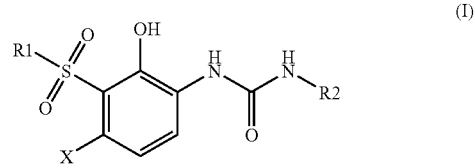

(I)

wherein

X is selected from the group consisting of halogen, $C_{1-3}$alkyl, $C_{1-3}$alkoxy, cyano, $CF_3$, and $OCF_3$;

R2 is selected from the group consisting of $C_{3-6}$cycloalkyl, phenyl and heteroaryl, wherein the phenyl or heteroaryl moieties are optionally substituted, once or twice, independently, by a substituent selected from the group consisting of $C_{1-3}$alkyl, halogen, $CF_3$, $OCF_3$, phenyloxy and benzyloxy; or phenyl substituted by methylenedioxy or by (di-halo-substituted)-methylenedioxy;

R1 is selected from the group consisting of the following ring systems (a-f):

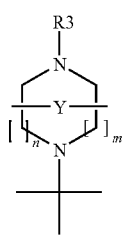

a)

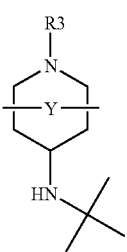

b)

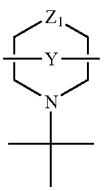

c)

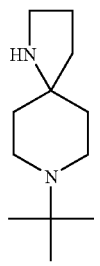

d)

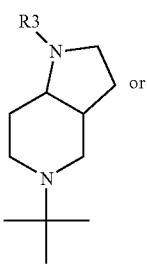

e) or

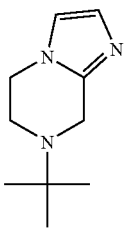

f)

wherein:

R3 is selected, independently, at each occurrence, from the group consisting of hydrogen, $C_{1-6}$alkyl, $C_{1-6}$alkoxy, $C_{3-7}$cycloalkyl, $C_{3-7}$cycloalkyl$C_{1-3}$-alkyl, phenyl, and phenyl$C_{1-3}$-alkyl, wherein the alkyl, cycloalkyl or phenyl moieties are optionally substituted, once or twice, independently, by a substituent selected from the group consisting of $C_{1-3}$alkyl, halogen, OH, $CF_3$, and $OCF_3$;

Y is a $C_{1-4}$-alkyl diradical attached to the ring system in two positions;

Z1 is selected from the group consisting of C=O, C=NOH and CHNR8;

R8 is selected from the group consisting of hydrogen, $C_{1-5}$alkyl, $C_{3-5}$cycloalkyl and $C_{3-5}$cycloalkyl$C_{1-5}$ alkyl;

m is an integer having a value of 1, 2 or 3; and n is an integer having a value of 1, 2 or 3;

or a pharmaceutically acceptable salt thereof.

As used herein, "alkyl" refers to a linear or branched saturated hydrocarbon group containing the specified number of carbon atoms, e.g., $C_{1-6}$alkyl means a straight or branched alkyl chain if at least 1, and at most 6, carbon atoms. The alkyl chain may be "optionally substituted" as defined hereinbelow. Examples of such groups include methyl, ethyl, n-propyl, isopropyl, n-butyl, isobutyl, sec-butyl, tert butyl, n-pentyl, isopentyl, neopentyl or hexyl and the like.

As used herein "cycloalkyl" refers to a saturated monocyclic hydrocarbon ring containing the specified number of carbon atoms, e.g., $C_{3-7}$cycloalkyl means a monocyclic hydrocarbon ring of 3 to 7 carbon atoms. Examples of such groups include cyclopropyl, cyclobutyl, cyclopentyl, cyclohexyl, cycloheptyl and the like.

As used herein "heteroaryl" refers to a 5-6 membered monocyclic aromatic ring containing 1 to 4 heteroatoms selected from oxygen, nitrogen and sulphur. Examples of such monocyclic aromatic rings include pyrrolyl, pyranyl, pyrazolyl, pyrimidyl, pyridazinyl, pyrazinyl, pyridyl, and the like.

As used herein, "halogen" or "halo" refers to F, Cl, Br or I.

As used herein, "$C_{1-3}$alkoxy" refers to a straight or branched alkoxy moiety containing 1 to 3 carbon atoms. Examples of alkoxy included herein are methoxy, ethoxy, propoxy and prop-2-oxy and the like.

As used herein, "optionally substituted," unless specifically defined, means substituted, independently, at each occurrence, one to three times, by such groups as halogen, $C_{1-3}$alkyl, $C_{1-3}$alkoxy, OH, heterocyclyl, and heteroaryl, such that the optional substituents may be further substituted, except for OH and halogen, one to three times, independently, by halogen or $C_{1-2}$alkyl.

The compounds of the present invention may contain one or more asymmetric carbon atoms and may exist in racemic and optically active forms. All of these compounds and diastereomers are contemplated to be within the scope of the present invention.

Suitably, X is selected from the group consisting of halogen, $C_{1-3}$alkyl, $C_{1-3}$alkoxy, cyano, $CF_3$, and $OCF_3$.

In one embodiment, X is halogen.

In another embodiment, X is selected from the group consisting of F, Cl and Br.

In another embodiment, X is Cl.

Suitably, R2 is selected from the group consisting of C3-6cycloalkyl, phenyl and heteroaryl, wherein the phenyl or heteroaryl moieties are optionally substituted, once or twice, independently, by a substituent selected from the group consisting of $C_{1-3}$alkyl, halogen, $CF_3$, $OCF_3$, phenyloxy and benzyloxy; or phenyl substituted by methylenedioxy or by (di-halo-substituted)-methylenedioxy.

In one embodiment, R2 represents phenyl, optionally substituted, independently, once or twice, by a substituent selected from the group consisting of $C_{1-3}$alkyl, halogen, $OCF_3$ or phenyloxy.

In another embodiment, R2 represents pyridyl, optionally substituted once by halogen.

In one embodiment, R2 represents pyridyl, optionally substituted once by chloro.

In another embodiment, R2 represents phenyl substituted by difluoromethylenedioxy.

In another embodiment, R2 represents $C_{3-6}$cycloalkyl.

In another embodiment, R2 represents halomethylphenyl, trihalomethyloxyphenyl, dihalophenyl, ethylphenyl or phenyloxyphenyl.

In another embodiment, R2 represents 3-fluoro-2-methylphenyl, 2-trifluoromethyloxyphenyl, 2-chloro-3-fluorophenyl, 2-ethylphenyl or 2-phenyloxyphenyl.

In another embodiment, R2 represents 3-fluoro-2-methylphenyl or 2-chloro-3-fluorophenyl.

In another embodiment, R2 represents halopyridyl.

In another embodiment, R2 represents 2-chloro-3-pyridyl.

Suitably, R1 is selected from the group consisting of the following ring systems (a-f):

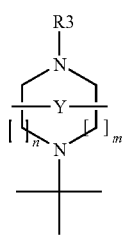
a)

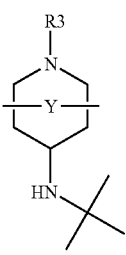
b)

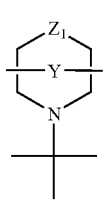
c)

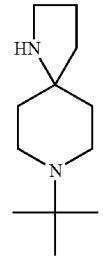
d)

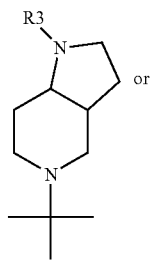
e)

or

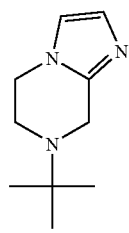
f)

wherein:

R3 is selected, independently, at each occurrence, from the group consisting of hydrogen, $C_{1-6}$alkyl, $C_{1-6}$alkoxy, $C_{3-7}$cycloalkyl, $C_{3-7}$cycloalkyl$C_{1-3}$-alkyl, phenyl and phenyl$C_{1-3}$-alkyl, wherein the alkyl, cycloalkyl or phenyl moieties are optionally substituted, once or twice, independently, by a substituent selected from the group consisting of $C_{1-3}$alkyl, halogen, OH, $CF_3$, and $OCF_3$;

Y is a $C_{1-4}$-alkyl diradical attached to the ring system in two positions;

Z1 is selected from the group consisting of C=O, C=NOH and CHNR8;

R8 is selected from the group consisting of hydrogen, $C_{1-5}$alkyl, $C_{3-5}$cycloalkyl and $C_{3-5}$cycloalkyl$C_{1-5}$ alkyl;

m is an integer having a value of 1, 2 or 3; and n is an integer having a value of 1, 2 or 3.

In one embodiment, Y is a $C_{1-2}$alkyl diradical.

In another embodiment, Y represents —$CH_2$—.

In another embodiment, Y represents —$C_2H_4$—.

In one embodiment, R3 on the R1 ring systems a), b) and e) is selected from the group consisting of hydrogen and $C_{1-4}$alkyl.

In another embodiment, R3 is selected from the group consisting of hydrogen, methyl, ethyl, propyl and butyl.

In another embodiment, R3 is cyclopropyl, cyclopropylmethyl, or phenylmethyl.

In one embodiment, R1 is selected from the group consisting of:

octahydro-5H-pyrrolo[3,2-c]pyridyl;
1-azabicyclo[2.2.2]octane-3-aminyl;
3,7-diazabicyclo[3.3.1]nonyl;
8-azabicyclo[3.2.1]octyl;
3-oxo-8-azabicyclo[3.2.1]octyl;
3-(hydroxyimino)-8-azabicyclo[3.2.1]octyl;

3,8-diazabicyclo[3.2.1]octyl;
3-(alkylamino)-8-azabicyclo[3.2.1]octyl;
5,6-dihydroimidazo[1,2-a]pyrazinyl;
3,8-diazabicyclo[3.2.1]octyl;
1,8-diazaspiro[4.5]decyl; and
2,5-diazabicyclo[2.2.1]heptyl;
optionally substituted, at the R3 value, by a substituent selected from the group consisting of $C_{1-6}$alkyl, $C_{1-6}$alkoxy, $C_{3-7}$cycloalkyl, $C_{3-7}$cycloalkyl$C_{1-3}$-alkyl, and aryl$C_{1-3}$-alkyl; and
optionally substituted at the R8 value by a substituent selected from the group consisting of $C_{1-5}$alkyl, $C_{3-5}$cycloalkyl and $C_{3-5}$cycloalkyl$C_{1-5}$ alkyl.

In another embodiment, R1 is selected from the group consisting of:
2,5-diazabicyclo[2.2.1]heptan-2-yl;
1,8-diazaspiro[4.5]decan-8-yl;
3,8-diazabicyclo[3.2.1]octan-3-yl;
5,6-dihydroimidazo[1,2-a]pyrazin-7(8H)-yl;
3-amino-8-azabicyclo[3.2.1]octane;
3,8-diazabicyclo[3.2.1]octan-3-yl;
3-(hydroxyimino)-8-azabicyclo[3.2.1]octan-8-yl;
3-oxo-8-azabicyclo[3.2.1]octan-8-yl;
8-azabicyclo[3.2.1]octan-3-aminyl;
3,7-diazabicyclo[3.3.1]nonan-3-yl;
1-azabicyclo[2.2.2]octan-3-aminyl; and
octahydro-5H-pyrrolo[3,2-c]pyridin-5-yl;
optionally substituted, at the R3 value, by a substituent selected from the group consisting of methyl, ethyl, propyl, butyl, $C_2H_4OH$, $C_3H_6OH$, cyclopropyl, cyclopropylmethyl, and phenylmethyl; and at the R8 value by a substituent selected from the group consisting of methyl, ethyl, propyl, butyl, cyclopropyl and cyclopropylmethyl.

In one embodiment, R1 is octahydro-5H-pyrrolo[3,2-c]pyridyl.

In another embodiment, R1 is 5,6-dihydroimidazo[1,2-a]pyrazinyl.

In another embodiment, R1 is 3,8-diazabicyclo[3.2.1]octyl or 2,5-diazabicyclo[2.2.1]heptyl.

Illustrative compounds of Formula (I) include:
N-{4-chloro-3-[(1S,4S)-2,5-diazabicyclo[2.2.1]hept-2-ylsulfonyl]-2-hydroxyphenyl}-N'-(2-chloro-3-fluorophenyl)urea;
N-(2-chloro-3-fluorophenyl)-N'-(4-chloro-2-hydroxy-3-{[(1S,4S)-5-methyl-2,5-diazabicyclo[2.2.1]hept-2-yl]sulfonyl}phenyl)urea;
N-{4-chloro-3-[(1S,4S)-2,5-diazabicyclo[2.2.1]hept-2-ylsulfonyl]-2-hydroxyphenyl}-N'-{2-[(phenylmethyl)oxy]phenyl}urea;
N-[4-chloro-3-(1,8-diazaspiro[4.5]dec-8-ylsulfonyl)-2-hydroxyphenyl]-N'-(3-fluoro-2-methylphenyl)urea;
N-{4-chloro-3-[(1R,5S)-3,8-diazabicyclo[3.2.1]oct-3-ylsulfonyl]-2-hydroxyphenyl}-N'-(2-chloro-3-fluorophenyl)urea;
N-{4-chloro-3-[(1S,4R)-2,5-diazabicyclo[2.2.1]hept-2-ylsulfonyl]-2-hydroxyphenyl}-N'-(2-chloro-3-fluorophenyl)urea;
N-[4-chloro-3-(5,6-dihydroimidazo[1,2-a]pyrazin-7(8H)-ylsulfonyl)-2-hydroxyphenyl]-N'-(2-chloro-3-fluorophenyl)urea;
N-[4-chloro-3-(1,8-diazaspiro[4.5]dec-8-ylsulfonyl)-2-hydroxyphenyl]-N'-(2-chloro-3-fluorophenyl)urea;
N-(2-chloro-3-fluorophenyl)-N'-(4-chloro-2-hydroxy-3-{[(1S,4S)-5-(2-hydroxyethyl)-2,5-diazabicyclo[2.2.1]hept-2-yl]sulfonyl}phenyl)urea;
N-{4-chloro-3-[(1S,4S)-2,5-diazabicyclo[2.2.1]hept-2-ylsulfonyl]-2-hydroxyphenyl}-N'-[2-(phenyloxy)phenyl]urea;
N-(4-chloro-2-hydroxy-3-{[(1S,4S)-5-methyl-2,5-diazabicyclo[2.2.1]hept-2-yl]sulfonyl}phenyl)-N'-{2-[(phenylmethyl)oxy]phenyl}urea;
N-(4-chloro-3-{[(1S,4S)-5-(cyclopropylmethyl)-2,5-diazabicyclo[2.2.1]hept-2-yl]sulfonyl}-2-hydroxyphenyl)-N'-(2-chloro-3-fluorophenyl)urea;
N-(4-chloro-2-hydroxy-3-{[(1R,5S)-3-(methylamino)-8-azabicyclo[3.2.1]oct-8-yl]sulfonyl}phenyl)-N'-(3-fluoro-2-methylphenyl)urea;
N-(4-chloro-3-{[(1R,5S)-3-(ethylamino)-8-azabicyclo[3.2.1]oct-8-yl]sulfonyl}-2-hydroxyphenyl)-N'-(3-fluoro-2-methylphenyl)urea;
N-(4-chloro-3-{[(1R,5S)-3-(cyclopropylamino)-8-azabicyclo[3.2.1]oct-8-yl]sulfonyl}-2-hydroxyphenyl)-N'-(2-chloro-3-fluorophenyl)urea;
N-[4-chloro-3-(3,8-diazabicyclo[3.2.1]oct-3-ylsulfonyl)-2-hydroxyphenyl]-N'-(3-fluoro-2-methylphenyl)urea;
N-(4-chloro-2-hydroxy-3-{[(1R,5S)-3-(hydroxyimino)-8-azabicyclo[3.2.1]oct-8-yl]sulfonyl}phenyl)-N'-(3-fluoro-2-methylphenyl)urea;
N-(4-chloro-3-{[(1R,5S)-3-(ethylamino)-8-azabicyclo[3.2.1]oct-8-yl]sulfonyl}-2-hydroxyphenyl)-N'-(2-chloro-3-fluorophenyl)urea;
N-[4-chloro-3-(3,8-diazabicyclo[3.2.1]oct-3-ylsulfonyl)-2-hydroxyphenyl]-N'-[2-(phenyloxy)phenyl]urea;
N-(3-{[(1R,5S)-3-(butylamino)-8-azabicyclo[3.2.1]oct-8-yl]sulfonyl}-4-chloro-2-hydroxyphenyl)-N'-(2-chloro-3-fluorophenyl)urea;
N-(3-{[(1R,5S)-3-(butylamino)-8-azabicyclo[3.2.1]oct-8-yl]sulfonyl}-4-chloro-2-hydroxyphenyl)-N'-(2-chloro-3-fluorophenyl)urea;
N-(4-chloro-2-hydroxy-3-{[(1R,5S)-3-oxo-8-azabicyclo[3.2.1]oct-8-yl]sulfonyl}phenyl)-N'-(3-fluoro-2-methylphenyl)urea;
N-(4-chloro-2-hydroxy-3-{[(1R,5S)-3-(propylamino)-8-azabicyclo[3.2.1]oct-8-yl]sulfonyl}phenyl)-N'-(3-fluoro-2-methylphenyl)urea;
N-[4-chloro-3-({(1R,5S)-3-[(cyclopropylmethyl)amino]-8-azabicyclo[3.2.1]oct-8-yl}sulfonyl)-2-hydroxyphenyl]-N'-(3-fluoro-2-methylphenyl)urea;
N-{4-chloro-3-[(1S,4S)-2,5-diazabicyclo[2.2.1]hept-2-ylsulfonyl]-2-hydroxyphenyl}-N'-(3-fluoro-2-methylphenyl)urea;
N-[4-chloro-3-(5,6-dihydroimidazo[1,2-a]pyrazin-7(8H)-ylsulfonyl)-2-hydroxyphenyl]-N'-(2-chloro-3-pyridinyl)urea;
N-(4-chloro-3-{[(1S,4S)-5-(cyclopropylmethyl)-2,5-diazabicyclo[2.2.1]hept-2-yl]sulfonyl}-2-hydroxyphenyl)-N'-(3-fluoro-2-methylphenyl)urea;
N-(2-chloro-3-fluorophenyl)-N'-(4-chloro-2-hydroxy-3-{[3-(phenylmethyl)-3,8-diazabicyclo[3.2.1]oct-8-yl]sulfonyl}phenyl)urea;
N-(3-{[(1R,5S)-3-(butylamino)-8-azabicyclo[3.2.1]oct-8-yl]sulfonyl}-4-chloro-2-hydroxyphenyl)-N'-(3-fluoro-2-methylphenyl)urea;
N-[4-chloro-3-(3,8-diazabicyclo[3.2.1]oct-3-ylsulfonyl)-2-hydroxyphenyl]-N'-(2-chloro-3-pyridinyl)urea;
N-{4-chloro-3-[(1R,4R)-2,5-diazabicyclo[2.2.1]hept-2-ylsulfonyl]-2-hydroxyphenyl}-N'-(2-chloro-3-pyridinyl)urea;
N-(2-chloro-3-fluorophenyl)-N'-(4-chloro-2-hydroxy-3-{[(1R,5S)-3-oxo-8-azabicyclo[3.2.1]oct-8-yl]sulfonyl}phenyl)urea;

N-(4-chloro-2-hydroxy-3-{[(1R,5S)-3-oxo-8-azabicyclo [3.2.1]oct-8-yl]sulfonyl}phenyl)-N'-(2-chloro-3-pyridinyl)urea;

N-(4-chloro-2-hydroxy-3-{[(1R,5R)-3-(phenylmethyl)-3,8-diazabicyclo[3.2.1]oct-8-yl]sulfonyl}phenyl)-N'-[2-(phenyloxy)phenyl]urea;

N-[4-chloro-3-(5,6-dihydroimidazo[1,2-a]pyrazin-7(8H)-ylsulfonyl)-2-hydroxyphenyl]-N'-(2-ethylphenyl)urea;

N-{4-chloro-3-[(1R,5S)-3,8-diazabicyclo[3.2.1]oct-8-ylsulfonyl]-2-hydroxyphenyl}-N'-(2-ethylphenyl)urea;

N-[4-chloro-3-(1,8-diazaspiro[4.5]dec-8-ylsulfonyl)-2-hydroxyphenyl]-N'-{2-[(trifluoromethyl)oxy]phenyl}urea;

6-chloro-3-({[(2-chloro-3-fluorophenyl)amino]carbonyl}amino)-2-hydroxy-N-[(3-endo)-8-methyl-8-azabicyclo[3.2.1]oct-3-yl]benzenesulfonamide;

N-(4-chloro-2-hydroxy-3-{[(1R,5S)-3-oxo-8-azabicyclo[3.2.1]oct-8-yl]sulfonyl}phenyl)-N'-(2,2-difluoro-1,3-benzodioxol-4-yl)urea;

N-{4-chloro-3-[(1R,5S)-3,8-diazabicyclo[3.2.1]oct-3-ylsulfonyl]-2-hydroxyphenyl}-N'-(2-ethylphenyl)urea;

N-[4-chloro-3-(1,8-diazaspiro[4.5]dec-8-ylsulfonyl)-2-hydroxyphenyl]-N'-(2-ethylphenyl)urea;

N-{4-chloro-3-[(1R,4R)-2,5-diazabicyclo[2.2.1]hept-2-ylsulfonyl]-2-hydroxyphenyl}-N'-(2-ethylphenyl)urea;

N-{4-chloro-3-[(1R,5S)-3,8-diazabicyclo[3.2.1]oct-8-ylsulfonyl]-2-hydroxyphenyl}-N'-{2-chloro-3-fluorophenyl}urea;

N-[(1R,5S)-8-azabicyclo[3.2.1]oct-3-yl]-6-chloro-3-({[(2-chloro-3-fluorophenyl)amino]carbonyl}amino)-2-hydroxybenzenesulfonamide;

N-{4-chloro-3-[(1S,5S)-3,7-diazabicyclo[3.3.1]non-3-ylsulfonyl]-2-hydroxyphenyl}-N'-(2-chloro-3-fluorophenyl)urea;

N-[(1R,5S)-8-azabicyclo[3.2.1]oct-3-yl]-6-chloro-2-hydroxy-3-[({[2-(phenyloxy)phenyl]amino}carbonyl)amino]benzenesulfonamide;

N-[(3S)-1-azabicyclo[2.2.2]oct-3-yl]-6-chloro-3-({[(2-chloro-3-fluorophenyl)amino]carbonyl}amino)-2-hydroxybenzenesulfonamide;

N-(4-chloro-2-hydroxy-3-{[(1R,5R)-8-(phenylmethyl)-3,8-diazabicyclo[3.2.1]oct-3-yl]sulfonyl}phenyl)-N'-(3-fluoro-2-methylphenyl)urea;

N-{4-chloro-3-[(1R,5S)-3,7-diazabicyclo[3.3.1]non-3-ylsulfonyl]-2-hydroxyphenyl}-N'-(2-chloro-3-pyridinyl)urea;

6-chloro-3-({[(3-fluoro-2-methylphenyl)amino]carbonyl}amino)-2-hydroxy-N-[(3-endo)-8-methyl-8-azabicyclo[3.2.1]oct-3-yl]benzenesulfonamide;

N-(2-chloro-3-fluorophenyl)-N'-[4-chloro-2-hydroxy-3-(octahydro-5H-pyrrolo[3,2-c]pyridin-5-ylsulfonyl)phenyl]urea;

N-[4-chloro-2-hydroxy-3-(octahydro-5H-pyrrolo[3,2-c]pyridin-5-ylsulfonyl)phenyl]-N'-(3-fluoro-2-methylphenyl)urea;

N-[4-chloro-2-hydroxy-3-(octahydro-5H-pyrrolo[3,2-c]pyridin-5-ylsulfonyl)phenyl]-N'-(2-chloro-3-pyridinyl)urea;

N-(4-chloro-3-{[(1S,4S)-5-(cyclopropylmethyl)-2,5-diazabicyclo[2.2.1]hept-2-yl]sulfonyl}-2-hydroxyphenyl)-N'-{2-[(phenylmethyl)oxy]phenyl}urea;

N-[(3-exo)-8-azabicyclo[3.2.1]oct-3-yl]-6-chloro-3-({[(2,2-difluoro-1,3-benzodioxol-4-yl)amino]carbonyl}amino)-2-hydroxybenzenesulfonamide; and N-[(1R,5S)-8-azabicyclo[3.2.1]oct-3-yl]-6-chloro-3-({[(3-fluoro-2-methylphenyl)amino]carbonyl}amino)-2-hydroxybenzenesulfonamide;

or a pharmaceutically acceptable salt thereof.

In another embodiment, the present invention involves compounds including:

N-{4-chloro-3-[(1R,5S)-3,8-diazabicyclo[3.2.1]oct-8-ylsulfonyl]-2-hydroxyphenyl}-N'-{2-chloro-3-fluorophenyl}urea;

N-{4-chloro-3-[(1S,4S)-2,5-diazabicyclo[2.2.1]hept-2-ylsulfonyl]-2-hydroxyphenyl}-N'-(2-chloro-3-fluorophenyl)urea;

N-(2-chloro-3-fluorophenyl)-N'-(4-chloro-2-hydroxy-3-{[(1S,4S)-5-methyl-2,5-diazabicyclo[2.2.1]hept-2-yl]sulfonyl}phenyl)urea;

N-{4-chloro-3-[(1S,4S)-2,5-diazabicyclo[2.2.1]hept-2-ylsulfonyl]-2-hydroxyphenyl}-N'-{2-[(phenylmethyl)oxy]phenyl}urea;

N-[4-chloro-3-(1,8-diazaspiro[4.5]dec-8-ylsulfonyl)-2-hydroxyphenyl]-N'-(3-fluoro-2-methylphenyl)urea;

N-{4-chloro-3-[(1R,5S)-3,8-diazabicyclo[3.2.1]oct-3-ylsulfonyl]-2-hydroxyphenyl}-N'-(2-chloro-3-fluorophenyl)urea;

N-{4-chloro-3-[(1S,4R)-2,5-diazabicyclo[2.2.1]hept-2-ylsulfonyl]-2-hydroxyphenyl}-N'-(2-chloro-3-fluorophenyl)urea;

N-[4-chloro-3-(5,6-dihydroimidazo[1,2-a]pyrazin-7(8H)-ylsulfonyl)-2-hydroxyphenyl]-N'-(2-chloro-3-fluorophenyl)urea;

N-[4-chloro-3-(1,8-diazaspiro[4.5]dec-8-ylsulfonyl)-2-hydroxyphenyl]-N'-(2-chloro-3-fluorophenyl)urea;

N-(2-chloro-3-fluorophenyl)-N'-(4-chloro-2-hydroxy-3-{[(1S,4S)-5-(2-hydroxyethyl)-2,5-diazabicyclo[2.2.1]hept-2-yl]sulfonyl}phenyl)urea;

N-{4-chloro-3-[(1S,4S)-2,5-diazabicyclo[2.2.1]hept-2-ylsulfonyl]-2-hydroxyphenyl}-N'-[2-(phenyloxy)phenyl]urea;

N-(4-chloro-2-hydroxy-3-{[(1S,4S)-5-methyl-2,5-diazabicyclo[2.2.1]hept-2-yl]sulfonyl}phenyl)-N'-{2-[(phenylmethyl)oxy]phenyl}urea;

N-(4-chloro-3-{[(1S,4S)-5-(cyclopropylmethyl)-2,5-diazabicyclo[2.2.1]hept-2-yl]sulfonyl}-2-hydroxyphenyl)-N'-(2-chloro-3-fluorophenyl)urea;

N-(4-chloro-2-hydroxy-3-{[(1R,5S)-3-(methylamino)-8-azabicyclo[3.2.1]oct-8-yl]sulfonyl}phenyl)-N'-(3-fluoro-2-methylphenyl)urea;

N-(4-chloro-3-{[(1R,5S)-3-(ethylamino)-8-azabicyclo[3.2.1]oct-8-yl]sulfonyl}-2-hydroxyphenyl)-N'-(3-fluoro-2-methylphenyl)urea;

N-(4-chloro-3-{[(1R,5S)-3-(cyclopropylamino)-8-azabicyclo[3.2.1]oct-8-yl]sulfonyl}-2-hydroxyphenyl)-N'-(2-chloro-3-fluorophenyl)urea;

N-[4-chloro-3-(3,8-diazabicyclo[3.2.1]oct-3-ylsulfonyl)-2-hydroxyphenyl]-N'-(3-fluoro-2-methylphenyl)urea;

N-(4-chloro-2-hydroxy-3-{[(1R,5S)-3-(hydroxyimino)-8-azabicyclo[3.2.1]oct-8-yl]sulfonyl}phenyl)-N'-(3-fluoro-2-methylphenyl)urea;

N-(4-chloro-3-{[(1R,5S)-3-(ethylamino)-8-azabicyclo[3.2.1]oct-8-yl]sulfonyl}-2-hydroxyphenyl)-N'-(2-chloro-3-fluorophenyl)urea;

N-[4-chloro-3-(3,8-diazabicyclo[3.2.1]oct-3-ylsulfonyl)-2-hydroxyphenyl]-N'-[2-(phenyloxy)phenyl]urea;

N-(3-{[(1R,5S)-3-(butylamino)-8-azabicyclo[3.2.1]oct-8-yl]sulfonyl}-4-chloro-2-hydroxyphenyl)-N'-(2-chloro-3-fluorophenyl)urea; and N-(4-chloro-2-hydroxy-3-{[(1R,5S)-3-oxo-8-azabicyclo[3.2.1]oct-8-yl]sulfonyl}phenyl)-N'-(3-fluoro-2-methylphenyl)urea;

or a pharmaceutically acceptable salt thereof.

In another embodiment, the present invention involves compounds selected from the group consisting of:

N-{4-chloro-3-[(1R,5S)-3,8-diazabicyclo[3.2.1]oct-8-ylsulfonyl]-2-hydroxyphenyl}-N'-{2-chloro-3-fluorophenyl}urea;

N-(4-chloro-3-{[(1S,4S)-5-(cyclopropylmethyl)-2,5-diazabicyclo[2.2.1]hept-2-yl]sulfonyl}-2-hydroxyphenyl)-N'-(2-chloro-3-fluorophenyl)urea;

N-(4-chloro-2-hydroxy-3-{[(1R,5S)-3-(methylamino)-8-azabicyclo[3.2.1]oct-8-yl]sulfonyl}phenyl)-N'-(3-fluoro-2-methylphenyl)urea;

N-(4-chloro-3-{[(1R,5S)-3-(ethylamino)-8-azabicyclo[3.2.1]oct-8-yl]sulfonyl}-2-hydroxyphenyl)-N'-(3-fluoro-2-methylphenyl)urea;

N-(4-chloro-3-{[(1R,5S)-3-(cyclopropylamino)-8-azabicyclo[3.2.1]oct-8-yl]sulfonyl}-2-hydroxyphenyl)-N'-(2-chloro-3-fluorophenyl)urea;

N-[4-chloro-3-(3,8-diazabicyclo[3.2.1]oct-3-ylsulfonyl)-2-hydroxyphenyl]-N'-(3-fluoro-2-methylphenyl)urea;

N-(4-chloro-2-hydroxy-3-{[(1R,5S)-3-(hydroxyimino)-8-azabicyclo[3.2.1]oct-8-yl]sulfonyl}phenyl)-N'-(3-fluoro-2-methylphenyl)urea;

N-(4-chloro-3-{[(1R,5S)-3-(ethylamino)-8-azabicyclo[3.2.1]oct-8-yl]sulfonyl}-2-hydroxyphenyl)-N'-(2-chloro-3-fluorophenyl)urea;

N-[4-chloro-3-(3,8-diazabicyclo[3.2.1]oct-3-ylsulfonyl)-2-hydroxyphenyl]-N'-[2-(phenyloxy)phenyl]urea;

N-(3-{[(1R,5S)-3-(butylamino)-8-azabicyclo[3.2.1]oct-8-yl]sulfonyl}-4-chloro-2-hydroxyphenyl)-N'-(2-chloro-3-fluorophenyl)urea; and N-(4-chloro-2-hydroxy-3-{[(1R,5S)-3-oxo-8-azabicyclo[3.2.1]oct-8-yl]sulfonyl}phenyl)-N'-(3-fluoro-2-methylphenyl)urea;

or a pharmaceutically acceptable salt thereof.

Methods of Preparation

The present invention provides a method of synthesizing a compound of Formula (I) comprising the steps of:

a) hydrolyzing a benzoxazole according to formula (II):

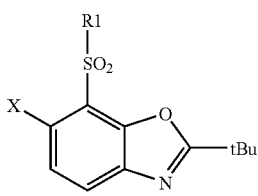
(II)

to form an aminophenol according to formula (III):

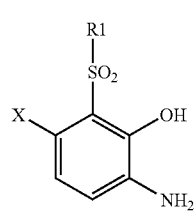
(III)

and b) exposing the aminophenol to an isocyanate or isocyanate precursor to form a final product according to formula (IV):

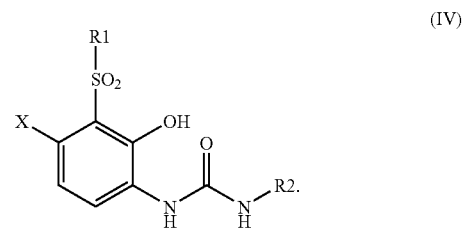
(IV)

The present invention also provides novel intermediates according to: formula (II):

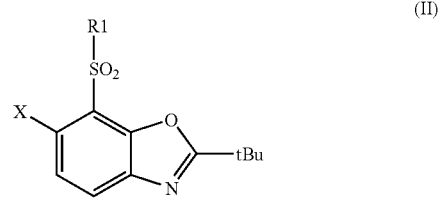
(II)

or (III):

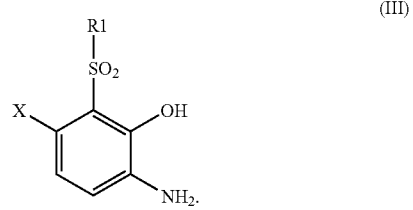
(III)

The compounds of Formulas (I) may be obtained by applying synthetic procedures, some of which are illustrated in the Scheme 1 below. The synthesis provided for in these Schemes is applicable for the producing compounds of Formulas (I) having a variety of different R1, R2 and X groups which are reacted, employing optional substituents which are suitably protected, to achieve compatibility with the reactions outlined herein.

Subsequent deprotection, in those cases, then affords compounds of the nature generally disclosed. Once the urea nucleus has been established, further compounds of these formulas may be prepared by applying standard techniques for functional group interconversion, well known in the art.

Scheme 1

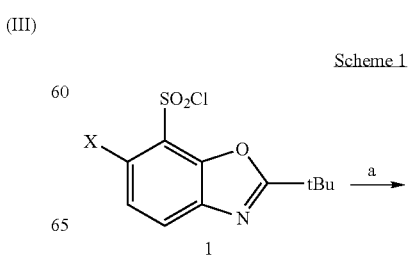

-continued

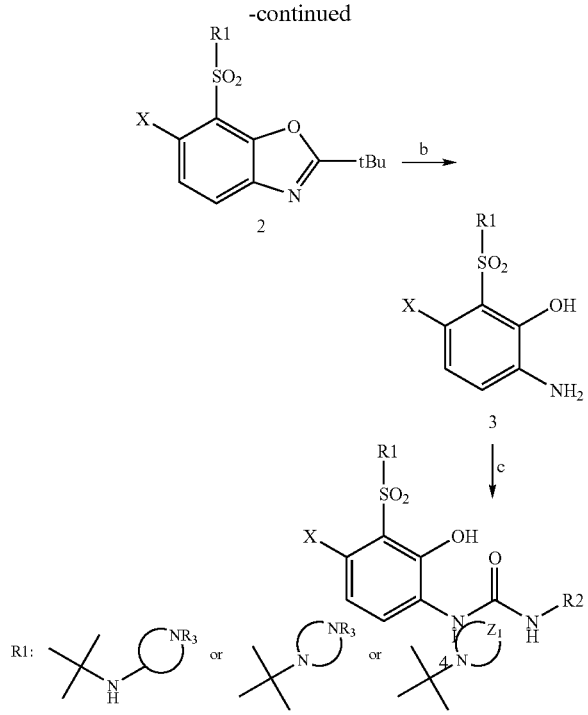

a) R1—H, Et₃N;
b) i) H₂SO₄/aq. 1,4-dioxane;
c) R2C=N=O or R2CON₃

In examples where R1 contain no amine functionality or a 30 or aromatic amine moiety or moieties, the compounds of Formula I may be prepared according to Scheme 1. The sulfonyl chloride 1 (prepared according to WO 01/68033A2, incorporated herein by reference to the extent required to synthesize Scheme 1, 1 compounds) is reacted with appropriate amine (R1-H) in the presence of a base such as Et₃N to form sulfonamide 2. Hydrolysis of the benzoxazole moiety yields the aminophenol 3 which, in turn, is exposed to an isocyanate or a suitable isocyanate precursor which may be transformed to the icocyanate in situ. This reaction produces the final urea 4. Compounds 2 and 3 represent novel intermediates in Scheme 1.

In cases where R1 contains a 1° or 2° Boc protected amine, the compounds can be prepared as outlined in Scheme 2. The sulfonamide formation and hydrolysis is performed as described above. However, since the latter will result in removal of the Boc group, it has to be reintroduced which can be accomplished under suitable conditions such as Boc anhydride and sodium hydroxide yielding compounds 3a. Following urea formation, the Boc group is then removed to for the desired product 5 under acidic conditions such as 4N hydrochloric acid in 1,4-dioxane. Finally, the resulting amines may be further elaborated an operation known to those skilled in the art as reductive amination to form 2° or 3° amine 6. Compounds 4a and 5 represent novel intermediates in Scheme 2.

Scheme 2

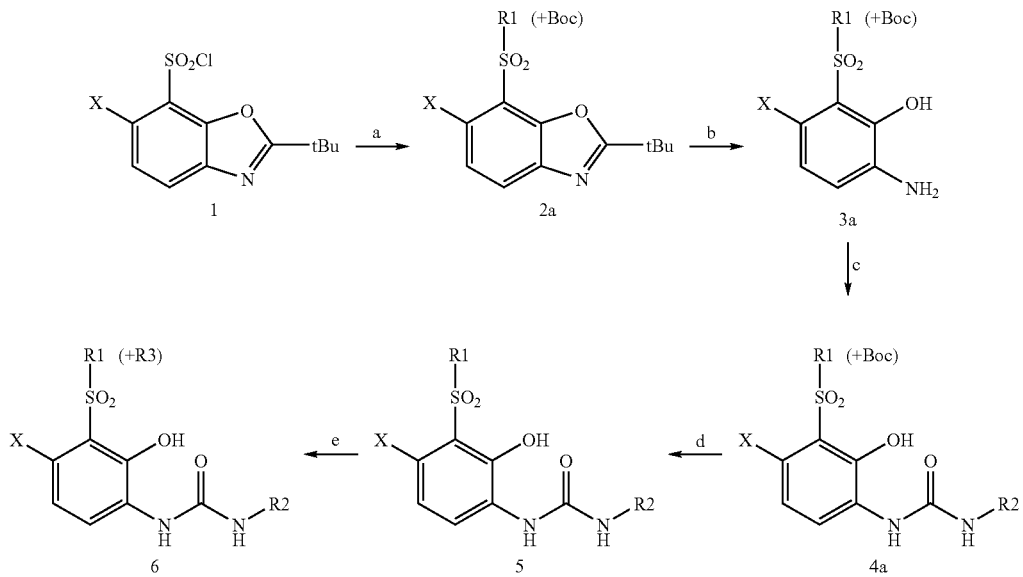

a) R1—H, Et₃N;
b) i) H₂SO₄/aq. 1,4-dioxane; ii) NaOH, Boc₂O;
c) R2C=N=O or R2CON₃
d) 4NHCl, 1,4-dioxane;
e) NaBH(OAc)₃, aldehyde or ketone Finally, in cases where R1 contains a ketone (i.e. Z1=C=O), the compound may also be elaborated by way of reductive amination by exposure to and amine in the presence of a reducing agent such as sodium triacetoxyborohydride, as represented in Scheme 3.

Scheme 3

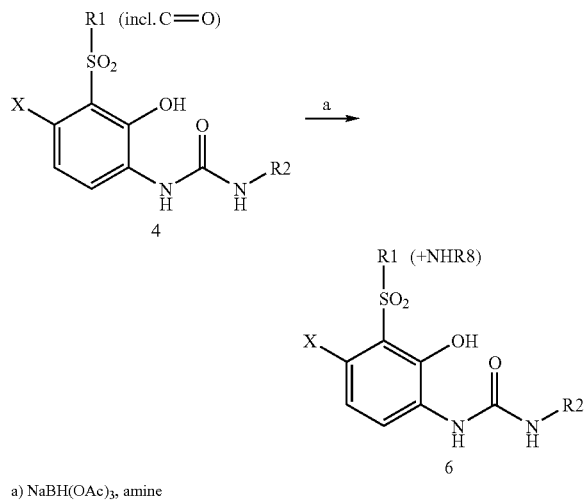

a) NaBH(OAc)₃, amine

SYNTHETIC EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

All references to ether are to diethyl ether; brine refers to a saturated aqueous solution of NaCl, DCM refers to dichloromethane, THF refers to tetrahydrofuran, EtOAc refers to ethyl acetate, Hex and Hx refers to hexane, IMS refers to industrial methylated spirit, TBME refers to tert-butylmethyl ether, DMF refers to dimethylformamide, BOC and Boc refers to tert-butyloxycarbonyl. Unless otherwise indicated, all temperatures are expressed in ° C. (degrees Centigrade). All reactions are conducted under an inert atmosphere at room temperature unless otherwise noted.

$^1$H NMR spectra were recorded on a Jeol Delta2 (300 MHz) spectrometer. Chemical shifts are expressed in parts per million (ppm, δ units). Splitting patterns describe apparent multiplicities and are designated as s (singlet), d (doublet), t (triplet), q (quartet), quint (quintet), m (multiplet), br (broad).

Unless otherwise stated, "flash" and "column chromatography" refers to flash column chromatography on silica using the stated solvent systems.

LC-MS data were obtained on either a PE Sciex Single Quadrupole LC/MS API-150 combined with a Shimadzu LC system (SCL-10A Controller and dual UV detector) or on a Waters micromass ZQ combined with a Waters 2695 separation module.

Starting Material 1

N-(3,4-dichlorophenyl)-2,2-dimethylpropanamide 3,4-dichloroaniline (150 g) was dissolved in 1.0 L TBME and the solution was cooled to 10° C. Sodium hydroxide (140.7 g of a 30% aqueous solution) was added under mechanical stirring. Pivaloyl chloride (125.9 mL) was added dropwise while keeping the internal temperature under 35° C. After the addition, the temperature of the reaction was maintained at 30-35° C. for a further 30 min. The reaction mixture was then allowed to cool to room temperature and subsequently kept at 0-5° C. for 1 h. The resulting precipitate was filtered of and washed with 600 mL water/MeOH (90/10) and then with 900 mL water. The resulting solid was the dried in a vacuum oven at 55° C. for 4 days. Yield: 162 g. $^1$H-NMR (DMSO-d$_6$) δ 9.46 (s, 1H), 8.04 (d, J=2.4 Hz, 1H), 7.65 (dd, J=9.0. 2.4 Hz, 1H), 7.54 (d, J=9.0 Hz, 1H), 1.22 (9H, s).

Starting Material 2

6-chloro-2-(1,1-dimethylethyl)-1,3-benzoxazole-7-sulfonyl chloride

N-(3,4-dichlorophenyl)-2,2-dimethylpropanamide (121 g) was dissolved in 720 mL THF and the solution was cooled to −50° C. Butyllithium (433 mL, 2.5N in hex) was added while keeping the internal temperature between −45° C. and −35° C. (final temp.: −35° C.) and held at −25° C. for 40 min. An hplc check of the reaction mixture revealed that 5-10% of the starting material remained. An additional 25 mL of butyllithium was added at −30° C. and the reaction was at −30 to −25° C. for a further 30 min (HPLC: no significant change). The reaction mixture was cooled to −45° C. and SO$_2$ was bubbled though the solution until saturation appeared to have been reached. Subsequently, the reaction mixture was at −10 to 0° C. for 45 min. Argon (2 double-balloon volumes) was bubbled through the solution following which the reaction mixture was cooled to −5° C. Sulfuryl chloride (58.8 mL) was added while keeping the temperature below 22° C. The reaction mixture was kept at 10-15° C. for 1 h (HPLC: complete). EtOAc was added and the mixture was concentrated, washed with water, saturated aqueous sodium bicarbonate and brine, dried over MgSO$_4$ and the solvent was evaporated in vacuo. The crude material crystallized and was triturated with hot hexane. Yield: 87.2 g $^1$H-NMR (DMSO-d$_6$) δ 7.60 (d, J=8.4 Hz, 1H), 7.34 (d, J=8.4 Hz, 1H), 1.43 (9H, s).

Intermediate 1: (General Procedure A)

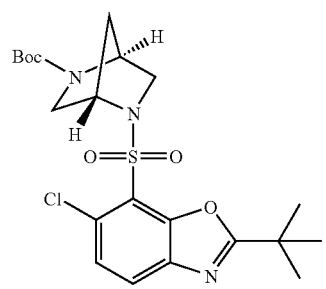

6-chloro-2-(1,1-dimethylethyl)-1,3-benzoxazole-7-sulfonyl chloride (25 g) was dissolved in 100 mL DCM and the solution was cooled to 0° C. Triethylamine (23 mL) was added followed by 1,1-dimethylethyl-(1S,4S)-2,5-diazabicyclo[2.2.1]heptane-2-carboxylate (16.8 g) dissolved in 25 mL DCM. The reaction mixture was stirred at 0° C. to room temperature for 14 h. The mixture was then diluted with EtOAc, washed with sat. aqueous sodium bicarbonate and brine. The organic layer was dried over MgSO$_4$, filtered and the solvent was removed in vacuo. The crude product was purified by filtration though a plug of silica gel eluting with EtOAc/Hex 1/1 yielding 22.1 g of pure product+14.0 g of impure material. LCMS (m/z, ES$^+$, M+H): 470.2.

Intermediate 2: (General Procedure B)

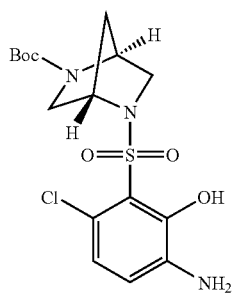

Intermediate 1 (1.43 g) was dissolved in dioxane (5 mL) and 50% (v/v) aqueous sulfuric acid (6 mL) was added. The reaction mixture was heated to reflux over night, allowed to cool to room temperature and the concentrated. The remaining material was basified with 50% (v/v) aqueous sodium hydroxide and then cooled on an ice bath. EtOAc (100 mL) followed by Boc$_2$O (0.69 g) was added and the mixture was then stirred at room temperature over night. The reaction mixture was then extracted twice with EtOAc and the combined organic layers were dried over MgSO$_4$ and concentrated in vacuo. The crude product was purified by column chromatography eluting with EtOAc/Hex 1/1. Yield: 1.1 g. LCMS (m/z, ES$^+$, M+H-tBu): 347.8.

Intermediate 3: (General Procedure C)

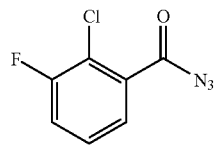

2-chloro-3-fluorobenzoic acid (0.79 g) was suspended in oxalyl chloride (10 mL) and then heated to reflux for 2 h. The reaction mixture was then cooled to room temperature and concentrated to dryness. The resulting material was dissolved in acetone (10 mL) and cooled to 0° C. Sodium azide (0.8 g) dissolved in water (5 mL) was added dropwise and the resulting mixture was stirred at 0° C. for 30 min and extracted with DCM. The organic layer was washed with water and brine, dried over Na$_2$SO$_4$ and concentrated. Yield: 0.6 g. The product was used without further characterization or purification.

Intermediate 4: (General Procedure D)

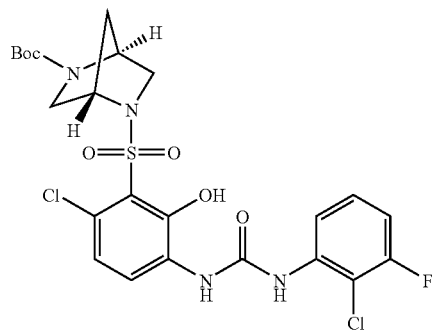

Intermediate 2 (1.1 g) was dissolved in DMF and intermediate 3 dissolved in DMF was added (total DMF volume: 15 mL). The reaction mixture was stirred at room temperature over night. TLC indicated that some unreacted intermediate 2 remained and thus an additional 0.64 g of intermediate 3 was added and stirring was continued at room temperature for 24 h. The reaction mixture was then extracted with EtOAc and the organic layer was washed with water, brine, dried over Na$_2$SO$_4$ and concentrated. The crude product was purified by column chromatography eluting with EtOAc/Hex 1/1. Yield: 1.3 g. LCMS (m/z, ES$^+$, M+H-tBu): 519.0.

Example 1

General Procedure E

N-[4-chloro-3-[(1S,4S)-2,5-diazabicyclo[2.2.1]hept-2-ylsulfonyl]-2-hydroxyphenyl]-N'-(2-chloro-3-fluorophenyl)urea

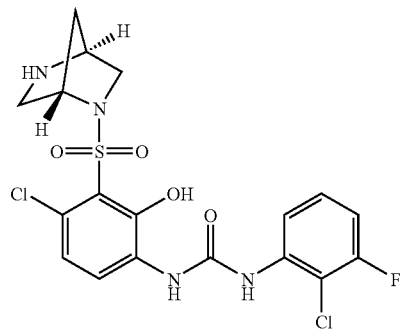

Intermediate 4 (1.3 g) was dissolved in 4N HCl in 1,4-dioxane (10 mL). The reaction mixture was stirred at room temperature for 2 h and then concentrated. The crude material was crystallized from MeOH/EtOAc, filtered, washed with EtOAc and then hexane. The material was then dried in a vacuum desiccator. Yield: 0.8 g. LCMS (m/z, ES$^+$, M+H): 475.0.

Example 2

General Procedure F

N-(4-chloro-3-{[(1S,4S)-5-(cyclopropylmethyl)-2,5-diazabicyclo[2.2.1]hept-2-yl]sulfonyl}-2-hydroxyphenyl)-N'-(2-chloro-3-fluorophenyl)urea

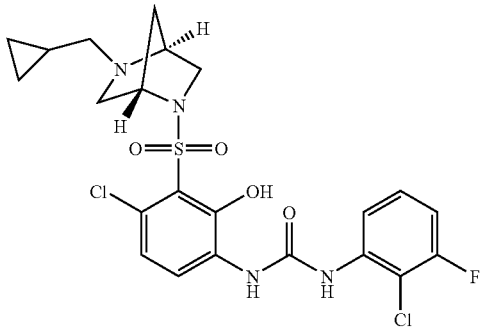

Example 1 (200 mg) was suspended in DCM (80 mL), cyclopropane carboxaldehyde (55 mg) was added and the mixture was stirred for 10 min before NaBH(OAc)$_3$ (0.37 g) was added. The reaction mixture was stirred at room temperature over night. The reaction was quenched by adding saturated aqueous sodium bicarbonate followed by stirring for 30 min. The mixture was then extracted with DCM and the organic layer was dried over Na$_2$SO$_4$ and concentrated. The crude product was purified by column chromatography eluting with 10% MeOH in DCM. Yield: 160 mg. MS (m/z, ES$^+$, M+H): 528.96.

Intermediate 5:

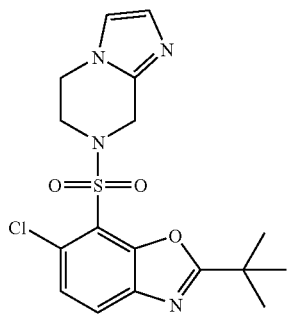

6-chloro-2-(1,1-dimethylethyl)-1,3-benzoxazole-7-sulfonyl chloride (457 mg) was dissolved in 2.5 mL DCM and the solution was cooled to 0° C. Triethylamine (0.41 mL) was added followed by 5,6,7,8-tetrahydroimidazo[1,2-a]pyrazine (201 mg) dissolved in 2.5 mL DCM. The reaction mixture was stirred at 0° C. to room temperature over night. The reaction was quenched with water and extracted with DCM (3×10 mL). The combined organic layers were dried Na$_2$SO$_4$, filtered and the solvent was removed in vacuo. The crude product was purified by column chromatography eluting with a gradient of 0 to 20% MeOH in DCM yielding 409 mg of product. R$_f$: 0.57 (10% MeOH in DCM).

Intermediate 6: (General Procedure G)

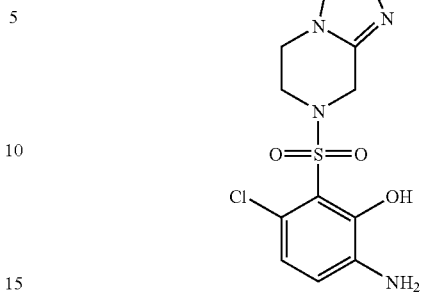

Intermediate 5 (409 mg) was dissolved in 5 mL IMS and 5 mL conc. HCl was added and the reaction mixture was heated at 60° C. for 3 days. The reaction was basified to pH 6 using saturated aqueous sodium hydroxide and then extracted with EtOAc (3×10 mL). The combined organic layers were dried Na$_2$SO$_4$, filtered and the solvent was removed in vacuo. The crude product was purified by column chromatography eluting with a gradient of 0 to 10% MeOH in DCM yielding 308 mg of product. R$_f$: 0.4 (10% MeOH in DCM). MS (m/z, ES$^+$, M+H): 328.98.

Intermediate 7:

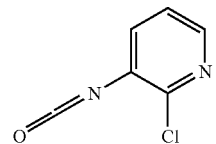

Triphosgene (7.7 g) in DCM (40 mL) was added to 3-amino-2-chloropyridine (10 g) in DCM (200 mL) and saturated aqueous NaHCO$_3$ (200 mL) at 0° C. The reaction was then left to stir for 1 h. The product was then extracted with DCM (2×50 mL), dried over Na$_2$SO$_4$ and the solvent removed in vacuo to yield an off-white solid. Trituration with hexane followed by filtration of the solids and removal of the solvent from the eluant yielded the product as a colorless oil. After flushing the product with argon and placing it in the refrigerator, a white crystalline solid appeared (6 g). $^1$H-NMR (CDCl$_3$) δ 8.22 (br s, 1H), 7.45 (d, 1H), 7.27-7.20 (m, 1H).

Example 3

General Procedure H

N-[4-chloro-3-(5,6-dihydroimidazo[1,2-a]pyrazin-7(8H)-ylsulfonyl)-2-hydroxyphenyl]-N'-(2-chloro-3-pyridinyl)urea

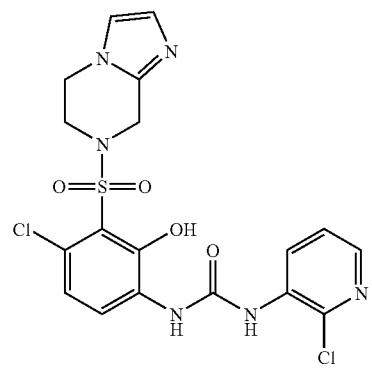

Intermediate 6 (50 mg) was dissolved in 2 mL DCM and intermediate 7 (30 mg) was added. The reaction mixture was stirred at room temperature for 3 d. The reaction was then quenched with MeOH and the solvent was removed in vacuo. The crude product was purified by column chromatography eluting with a gradient of 0 to 20% MeOH in DCM and then triturated with MeOH containing a few drops of DCM yielding 30 mg of product. $R_f$: 0.13 (5% MeOH in DCM). MS (m/z, ES$^+$, M+H): 482.90.

Intermediate 8:

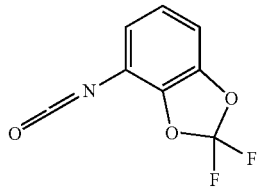

Two batches of 2,2-difluoro-1,3-benzodioxol-4-amine (1 g and 3.58 g) were treated with triphosgene (566 mg and 2.04 mg) and saturated aqueous NaHCO$_3$ (20 mL and 80 mL) in DCM (20 mL and 80 mL) according to the procedure described for Intermediate 9 yielding 3.27 g of the desired product after the 2 batches had been combined. $^1$H-NMR (CDCl$_3$) δ 7.05 (t, 1H), 6.90 (d, 1H), 6.82 (d, 1H).

Intermediate 9:

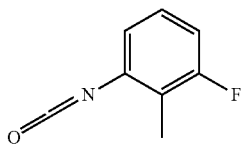

3-fluoro-2-methylaniline (7.4 g) was dissolved in DCM (220 mL) at room temperature under an argon atmosphere. After cooling to 0° C., aqueous saturated NaHCO$_3$ (220 mL) was added followed by triphosgene (5.85 g). The reaction was left to stir at 0° C. for 1 h. After this time, the product was extracted with DCM (2×50 mL). The organic fractions were combined, dried over MgSO$_4$ and the solvent removed in vacuo to yield a yellow oil. Addition of hexane allowed precipitation of a white salt which was filtered off. Removal of the hexane in vacuo yielded a yellow oil (7.69 g, 86%). $^1$H-NMR (CDCl$_3$) δ 7.09 (dd, 1H), 6.92-6.85 (m, 2H), 2.24 (s, 3H).

Intermediate 10:

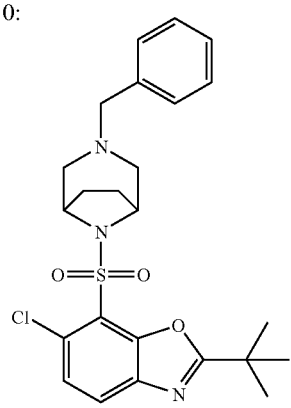

6-chloro-2-(1,1-dimethylethyl)-1,3-benzoxazole-7-sulfonyl chloride (3.06 g) was dissolved in 70 mL THF and the solution was cooled to 0° C. Triethylamine (2.77 mL) was added followed by 3-(benzyl)-3,8-diazabicyclo[3.2.1]octane (2.41 g, prepared according to EP266576 (A2,A3)). The reaction mixture was stirred at 0° C. to room temperature for 14 h. The reaction was quenched with water and extracted with EtOAc (3×100 mL), washed with sat. aqueous sodium bicarbonate and brine. The combined organic layers were dried over Na$_2$SO$_4$, filtered and the solvent was removed in vacuo. The crude product triturated with hexane to give an off-white solid. Yield: 4.17 g. $R_f$: 0.88 (10% MeOH in DCM).

Intermediate 11:

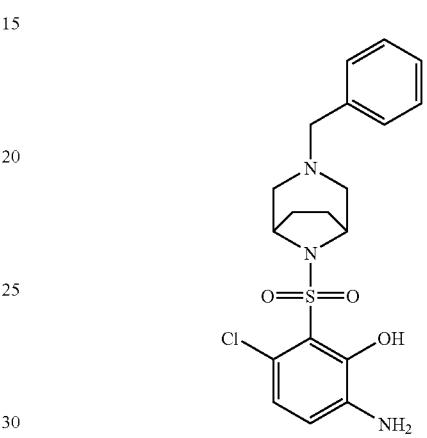

Intermediate 10 (4.17 g) was dissolved in 42 mL ethanol and 42 mL conc. HCl was added and the reaction mixture was heated at 70° C. for 3 days. The reaction was basified to pH7 using 2M aqueous sodium hydroxide and NH$_4$HCO$_3$. All solvent was removed in vacuo and the resulting solid was washed with EtOAc until TLC showed that all product had been extracted. The solvent was removed in vacuo and the crude product was purified by column chromatography eluting with a gradient of 2 to 9% MeOH in DCM yielding 3.13 g of product. $R_f$: 0.75 (10% MeOH in DCM)

Intermediate 12:

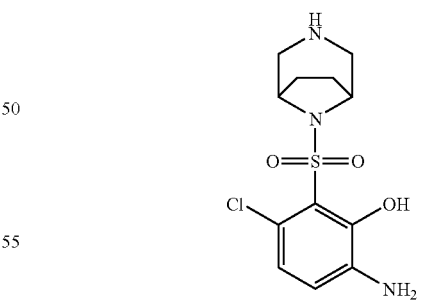

Intermediate 11 (1.09 g) was dissolved in 5 mL EtOAc, Pd(OH)$_2$ (250 mg) was added and the mixture was stirred and H$_2$ atmosphere (near atmospheric pressure) for 1.5d. The reaction mixture was filtered through celite and the solvent was removed in vacuo. The product was isolated by column chromatography eluting with a gradient of 0 to 100% MeOH in DCM yielding 34 m g of product. (recovered starting material: 522 mg). $R_f$: 0.75 (10% MeOH in DCM).

Intermediate 13:

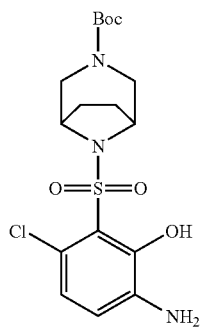

Intermediate 12 (198 mg) was dissolved in THF (5 mL) and the mixture was cooled to 0° C. Triethylamine (191 uL) was added followed by (Boc)₂O (135 mg). The reaction mixture was stirred at 0° C. to room temperature over night. The reaction was quenched with water and the product was extracted with EtOAc (3×10 mL). The combined organic layers were dried over Na₂SO₄, filtered and the solvent was removed in vacuo. The crude product was purified by column chromatography eluting with a gradient of 9 to 100% EtOAc in hexane. Yield: 168 mg. $R_f$: 0.5 (EtOAc/Hex 1/1).

Intermediate 14:

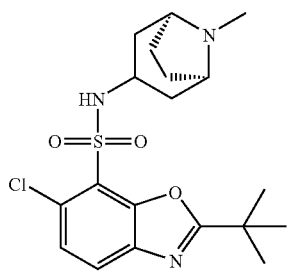

6-chloro-2-(1,1-dimethylethyl)-1,3-benzoxazole-7-sulfonyl chloride (1.0 g) was dissolved in 10 mL DCM and the solution was cooled to 0° C. 8-methyl-8-azabicyclo[3.2.1]octan-3-amine (0.90 g) was added dropwise and the reaction mixture was stirred at room temperature for 3 h. The reaction was quenched with water and extracted with DCM (×2). The combined organic layer was dried over Na₂SO₄, filtered and the solvent was removed in vacuo. The crude product was purified by filtration though a plug of silica gel eluting a gradient of 0 to 100% MeOH in DCM yielding 1.20 g. $R_f$: 0.26 (10% MeOH in DCM).

Intermediate 15: (General Procedure I)

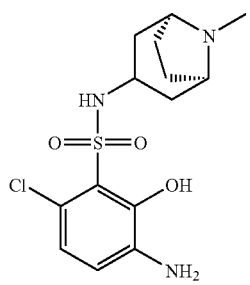

Intermediate 14 (0.6 g) was dissolved in 3 mL THF, 4 mL conc. HCl was added and the reaction mixture was heated at 90° C. over night. The reaction mixture was poured into ice water, EtOAc was added and the mixture was basified to pH 12 by addition of 2N NaOH. The organic layer was dried over Na₂SO₄, filtered and the solvent was removed in vacuo. Ether was added yielding a grey solid. The ether was decanted off and the solid was dried. Yield: 0.35 g. LCMS (m/z, ES⁺, M+H): 346.07

Intermediate 16:

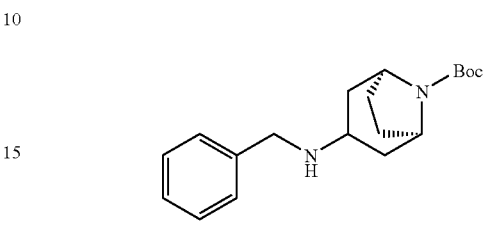

N-Boc-tropinone (4.5 g) and benzylamine (3.27 mL) was dissolved in 50 mL DCM and the mixture was cooled to 0° C. Sodium triacetoxyborohydride (6.35 g) was added and the reaction mixture was stirred at room temperature over night. The reaction was quenched with water (50 mL) extracted with DCM (3×20 mL). The combined organic layers were dried over Na₂SO₄, filtered and the solvent was removed in vacuo. The crude product was purified by column chromatography eluting with a gradient of 0 to 50% MeOH in DCM yielding 5.08 g of product. $R_f$: 0.43 (10% MeOH in DCM).

Intermediate 17:

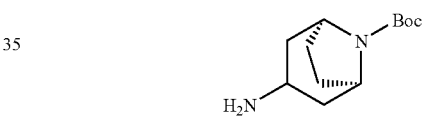

An Autoclave was charged with Intermediate 16 (5 g) and Pd(OH)₂ (500 mg) dissolved/suspended in MeOH (60 mL) and subjected to a 70 psi hydrogen atmosphere. The autoclave was first heated to 100° C. for 2 h and then room temperature over night. The reaction mixture was filtered through celite which was washed with MeOH (2×100 mL). The methanol solutions were combined and the solvent was removed in vacuo. Yield: 3.7 g. $R_f$: 0.30 (20% MeOH in DCM).

Intermediate 18:

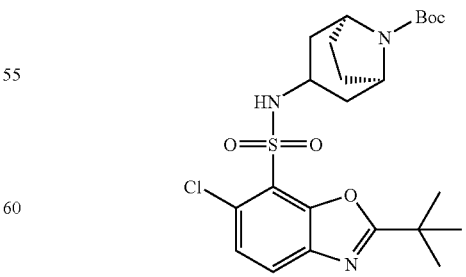

Intermediate 1 (4.2 g) and intermediate 17 (3.7 g) were subjected to the conditions of general procedure (A) yielding 4.76 g of the desired product. $R_f$: 0.60 (EtOAc/Hex 1/1).

Intermediate 19: (General Procedure J)

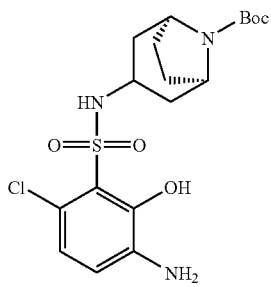

Intermediate 18 (4.76 g) was dissolved in 50 mL IMS, conc. HCl (50 mL) was added and the reaction mixture was heated to 70° C. over night. Solvent was removed in vacuo and the remaining material was basified to pH 14 with 2M sodium hydroxide. EtOAc (10 mL) was added followed by (Boc)$_2$O (2.29 g). The resulting mixture was stirred at room temperature for 3 d. The aqueous layer was extracted with EtOAc (2×50 mL) and the combined organic layers were dried over Na$_2$SO$_4$, filtered and the solvent was removed in vacuo. The crude product was purified by column chromatography eluting with a gradient of 0 to 10% MeOH in DCM yielding 3.79 g of product. R$_f$: 0.63 (5% MeOH in DCM).

Intermediate 20:

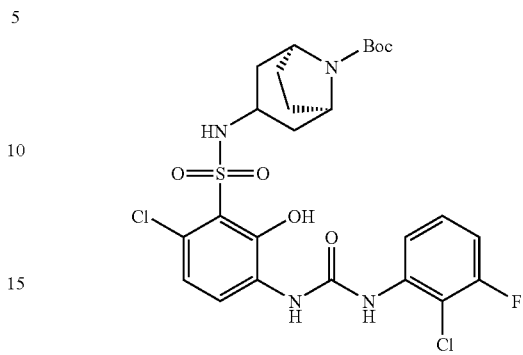

Intermediate 19 (500 mg) and intermediate 3 (346 mg) were dissolved in DCM (6 mL) the reaction mixture was stirred at room temperature over night. The solvent was removed in vacuo and the crude product was triturated with ether containing a small amount of MeOH yielding 610 mg of an off-white solid. R$_f$: 0.50 (EtOAc/Hex 1/2).

TABLE 1

Examples prepared according to the general procedures described above

| Ex. | Structure | IUPAC Name | Preparation: Starting materials (General Procedures) | Characterization |
|---|---|---|---|---|
| 4 | 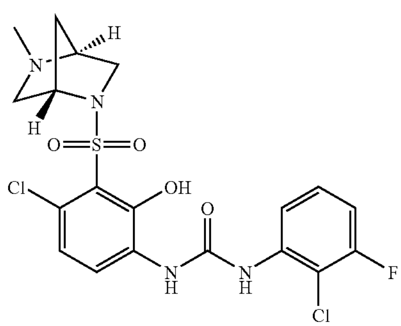 | N-(2-chloro-3-fluorophenyl)-N'-(4-chloro-2-hydroxy-3-{[(1S,4S)-5-methyl-2,5-diazabicyclo[2.2.1]hept-2-yl]sulfonyl}phenyl)urea | Example 1, Formaldehyde (F) | LCMS (m/z, ES$^+$, M + H): 488.95 |
| 5 | 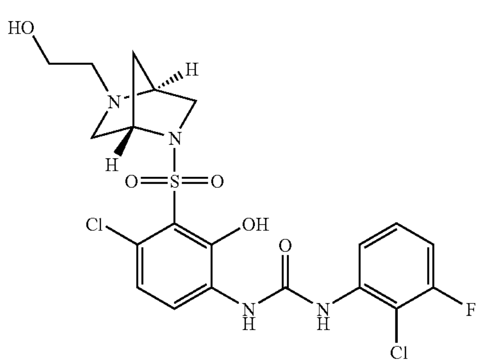 | N-(2-chloro-3-fluorophenyl)-N'-(4-chloro-2-hydroxy-3-{[(1S,4S)-5-(2-hydroxyethyl)-2,5-diazabicyclo[2.2.1]hept-2-yl]sulfonyl}phenyl)urea | Example 1, Glycoaldehyde-dimer (F) | LCMS (m/z, ES$^+$, M + H): 518.96 |

TABLE 1-continued

Examples prepared according to the general procedures described above

| Ex. | Structure | IUPAC Name | Preparation: Starting materials (General Procedures) | Characterization |
|---|---|---|---|---|
| 6 | 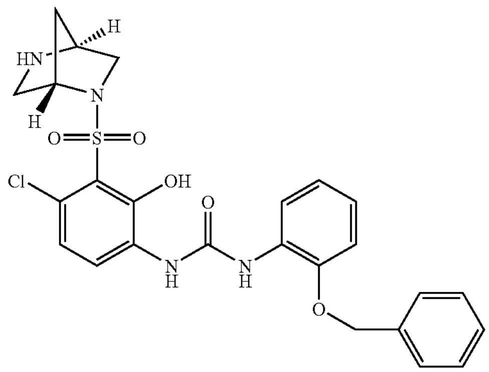 | N-{4-chloro-3-[(1S,4S)-2,5-diazabicyclo[2.2.1]hept-2-ylsulfonyl]-2-hydroxyphenyl}-N'-{2-[(phenylmethyl)oxy]phenyl}urea | Intermediate 2, 2-(benzyloxy)-benzoic acid. (C, D, E) | LCMS (m/z, ES$^+$, M + H): 529.05 |
| 7 | 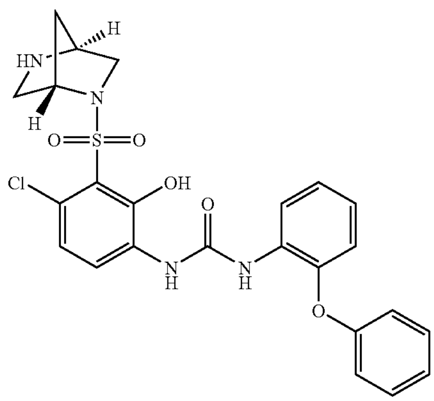 | N-{4-chloro-3-[(1S,4S)-2,5-diazabicyclo[2.2.1]hept-2-ylsulfonyl]-2-hydroxyphenyl}-N'-[2-(phenyloxy)phenyl]urea | Intermediate 2, 2-phenoxyphenyl isocyanate (D, E) | LCMS (m/z, ES$^+$, M + H): 515.03 |
| 8 | 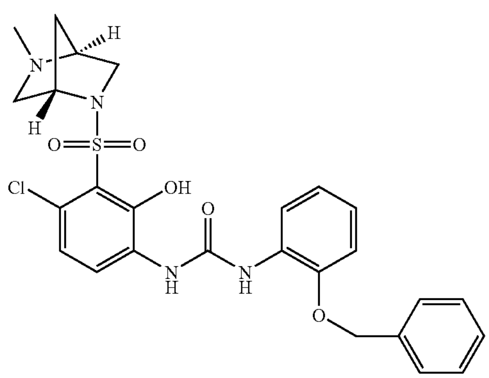 | N-(4-chloro-2-hydroxy-3-{[(1S,4S)-5-methyl-2,5-diazabicyclo[2.2.1]hept-2-yl]sulfonyl}phenyl)-N'-{2-[(phenylmethyl)oxy]phenyl}urea | Example 6, formaldehyde (F) | LCMS (m/z, ES$^+$, M + H): 543.05 |
| 9 | 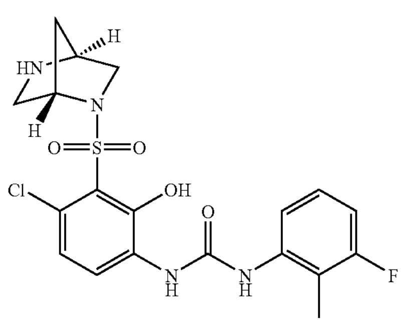 | N-{4-chloro-3-[(1S,4S)-2,5-diazabicyclo[2.2.1]hept-2-ylsulfonyl]-2-hydroxyphenyl}-N'-(3-fluoro-2-methylphenyl)urea | Intermediate 2, Intermediate 9 (H, E) | LCMS (m/z, ES$^+$, M + H): 455.02 |

TABLE 1-continued

Examples prepared according to the general procedures described above

| Ex. | Structure | IUPAC Name | Preparation: Starting materials (General Procedures) | Characterization |
|---|---|---|---|---|
| 10 | 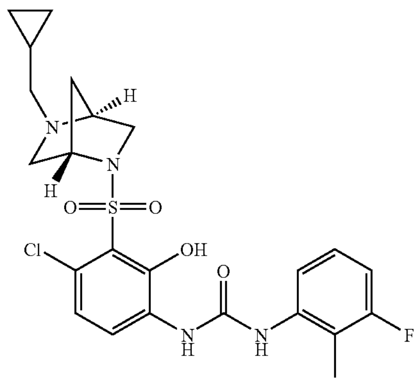 | N-(4-chloro-3-{[(1S,4S)-5-(cyclopropylmethyl)-2,5-diazabicyclo[2.2.1]hept-2-yl]sulfonyl}-2-hydroxyphenyl)-N'-(3-fluoro-2-methylphenyl)urea | Example 9, Cyclopropyl-carboxaldehyde (F) | LCMS (m/z, ES+, M + H): 509.06 |
| 11 | 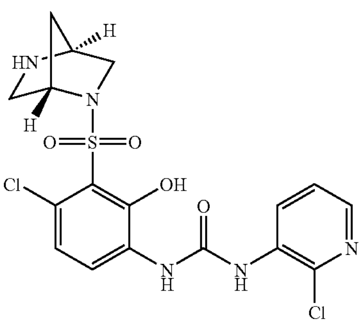 | N-{4-chloro-3-[(1R,4R)-2,5-diazabicyclo[2.2.1]hept-2-ylsulfonyl]-2-hydroxyphenyl}-N'-(2-chloro-3-pyridinyl)urea | Intermediate 2, Intermediate 7 (H, E) | LCMS (m/z, ES+, M + H): 457.95 |
| 12 | 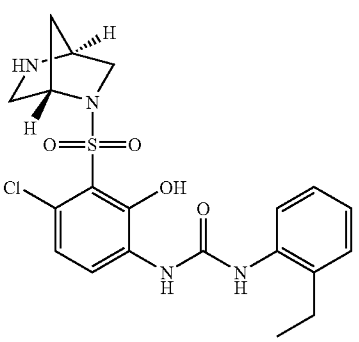 | N-{4-chloro-3-[(1R,4R)-2,5-diazabicyclo[2.2.1]hept-2-ylsulfonyl]-2-hydroxyphenyl}-N'-(2-ethylphenyl)urea | Intermediate 2, 2-ethylphenyl isocyanate (H, E) | LCMS (m/z, ES+, M + H): 451.02 |
| 13 | 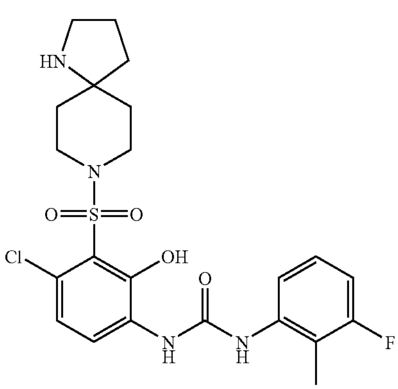 | N-[4-chloro-3-(1,8-diazaspiro[4.5]dec-8-ylsulfonyl)-2-hydroxyphenyl]-N'-(3-fluoro-2-methylphenyl)urea | Starting material 2, 8-Diaza-spiro[4.5]decane-1-carboxylic acid tert-butyl ester, Intermediate 9, (A, B, H, E) | LCMS (m/z, ES+, M + H): 496.97 |

TABLE 1-continued

Examples prepared according to the general procedures described above

| Ex. | Structure | IUPAC Name | Preparation: Starting materials (General Procedures) | Characterization |
|---|---|---|---|---|
| 14 | 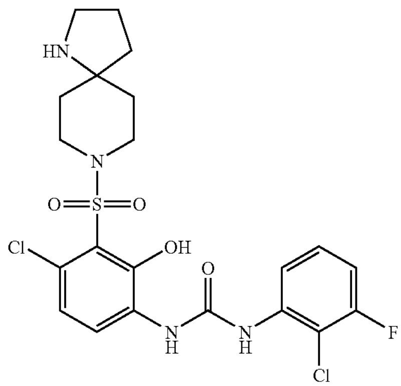 | N-[4-chloro-3-(1,8-diazaspiro[4.5]dec-8-ylsulfonyl)-2-hydroxyphenyl]-N'-(2-chloro-3-fluorophenyl)urea | Starting material 2, 8-Diaza-spiro[4,5]decane-1-carboxylic acid tert-butyl ester, 2-chloro-3-fluorophenyl isocyanate (A, B, H, E) | LCMS (m/z, ES+, M + H): 516.97 |
| 15 | 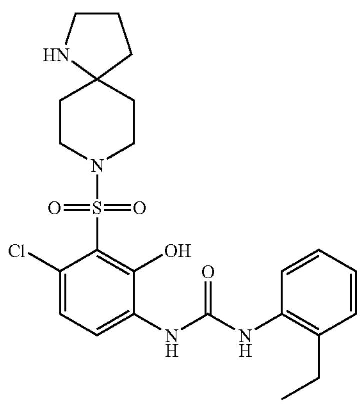 | N-[4-chloro-3-(1,8-diazaspiro[4.5]dec-8-ylsulfonyl)-2-hydroxyphenyl]-N'-(2-ethylphenyl)urea | Starting material 2, 8-Diaza-spiro[4,5]decane-1-carboxylic acid tert-butyl ester, 2-ethylphenyl isocyanate (A, B, H, E) | LCMS (m/z, ES+, M + H): 492.96 |
| 16 | 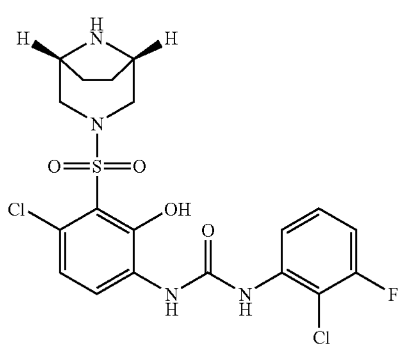 | N-{4-chloro-4-[(1R,5S)-3,8-diazabicyclo[3.2.1]oct-3-ylsulfonyl]-2-hydroxyphenyl}-N'-(2-chloro-3-fluorophenyl)urea | Starting material 2 8-Boc-3,8-diaza-bicyclo[3.2.1]-octane, 2-chloro-3-fluorophenyl isocyanate (A, B, H, E) | LCMS (m/z, ES+, M + H): 492.96 |
| 17 | 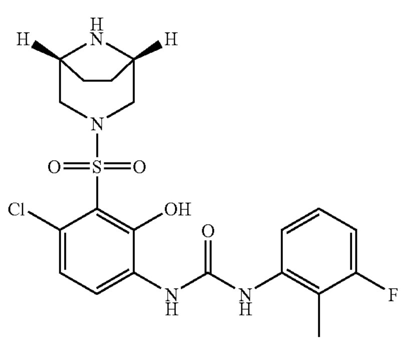 | N-[4-chloro-3-(3,8-diazabicyclo[3.2.1]oct-3-ylsulfonyl)-2-hydroxyphenyl]-N'-(3-fluoro-2-methylphenyl)urea | Starting material 2, 8-Boc-3,8-diaza-bicyclo[3.2.1]-octane, Intermediate 9, (A, B, H, E) | LCMS (m/z, ES+, M + H): 468.98 |

TABLE 1-continued

Examples prepared according to the general procedures described above

| Ex. | Structure | IUPAC Name | Preparation: Starting materials (General Procedures) | Characterization |
|---|---|---|---|---|
| 18 | 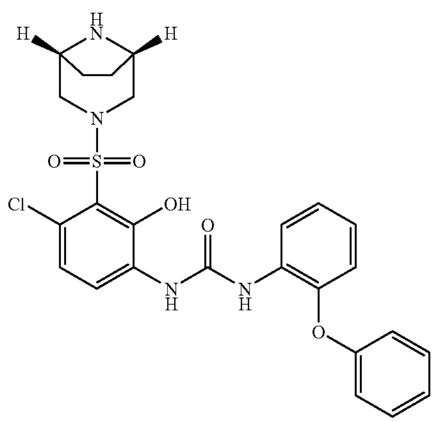 | N-[4-chloro-3-(3,8-diazabicyclo[3.2.1]oct-3-ylsulfonyl)-2-hydroxyphenyl]-N'-[2-(phenyloxy)phenyl]urea | Starting material 2, 8-Boc-3,8-diaza-bicyclo[3.2.1]-octane, 2-phenoxyphenyl isocyanate, (A, B, H, A) | LCMS (m/z, ES+, M + H): 528.98 |
| 19 | 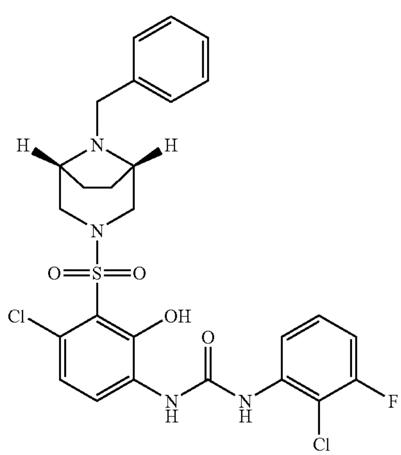 | N-(2-chloro-3-fluorophenyl)-N'-(4-chloro-2-hydroxy-3-{[3-(phenylmethyl)-3,8-diazabicyclo[3.2.1]oct-8-yl]sulfonyl}phenyl)urea | Intermediate 11, 2-chloro-3-fluorophenyl isocyanate, (H) | LCMS (m/z, ES+, M + H): 579.20 |
| 20 | 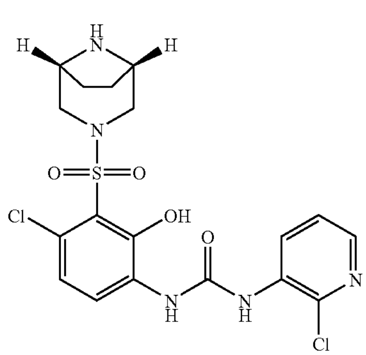 | N-[4-chloro-3-(3,8-diazabicyclo[3.2.1]oct-3-ylsulfonyl)-2-hydroxyphenyl]-N'-(2-chloro-3-pyridinyl)urea | Starting material 2, 8-Boc-3,8-diaza-bicyclo[3.2.1]-octane, intermeduate 7, (A, B, H, E) | LCMS (m/z, ES+, M + H): 471.89 |

TABLE 1-continued

Examples prepared according to the general procedures described above

| Ex. | Structure | IUPAC Name | Preparation: Starting materials (General Procedures) | Characterization |
|---|---|---|---|---|
| 21 | 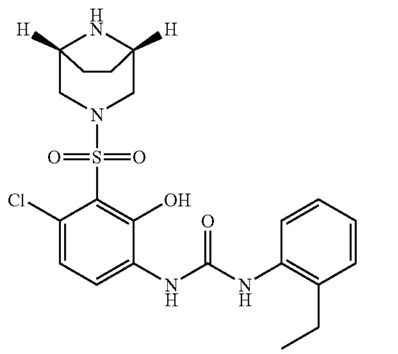 | N-{4-chloro-3-[(1R,5S)-3,8-diazabicyclo[3.2.1]oct-3-ylsulfonyl]-2-hydroxyphenyl}-N'-(2-ethylphenyl)urea | Starting material 2, 8-Boc-3,8-diaza-bicyclo[3.2.1]-octane, 2-ethylphenyl isocyanate, (A, B, H, E) | LCMS (m/z, ES+, M + H): 465.07 |
| 22 | 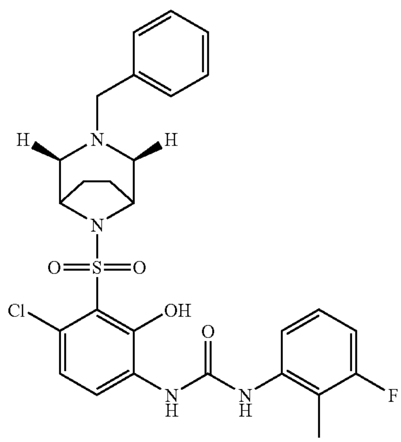 | N-(4-chloro-2-hydroxy-3-{[3-(phenylmethyl)-3,8-diazabicyclo[3.2.1]oct-8-yl]sulfonyl}phenyl)-N'-(3-fluoro-2-methylphenyl)urea | Intermediate 11, Intermediate 9, (H) | LCMS (m/z, ES+, M + H): 559.17 |
| 23 | 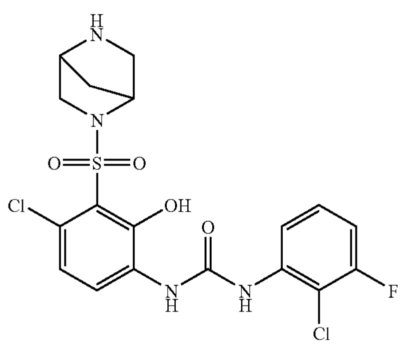 | (+/−)-N-[4-chloro-3-(2,5-diazabicyclo[2.2.1]hept-2-ylsulfonyl)-2-hydroxyphenyl]-N'-(2-chloro-3-fluorophenyl)urea | Starting material 2, (+/−)-1,1-dimethylethyl-2,5-diazabicyclo[2.2.1]heptane-2-carboxylate 2-chloro-3-fluorophenyl isocyanate, (A, B, H, E) | LCMS (m/z, ES+, M + H): 474.95 |
| 24 | 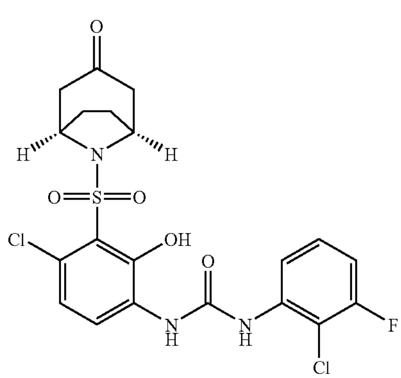 | N-(2-chloro-3-fluorophenyl)-N'-(4-chloro-2-hydroxy-3-{[(1R,5S)-3-oxo-8-azabicyclo[3.2.1]oct-8-yl]sulfonyl}phenyl)urea | Starting material 2, Tropanone, 2-chloro-3-fluorophenyl isocyanate, (A, G, H) | LCMS (m/z, ES+, M + H): 502.00 |

TABLE 1-continued

Examples prepared according to the general procedures described above

| Ex. | Structure | IUPAC Name | Preparation: Starting materials (General Procedures) | Characterization |
|---|---|---|---|---|
| 25 | 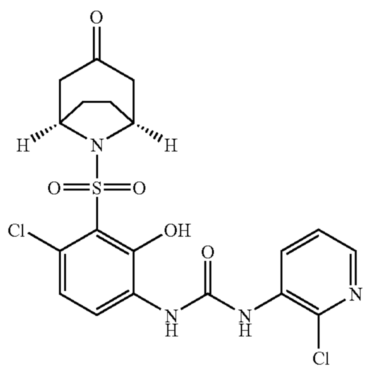 | N-(4-chloro-2-hydroxy-3-{[(1R,5S)-3-oxo-8-azabicyclo[3.2.1]oct-8-yl]sulfonyl}phenyl)-N'-(2-chloro-3-pyridinyl)urea | Starting material 2, Tropanone, Intermediate 7, (A, G, H) | LCMS (m/z, ES+, M + H): 484.94 |
| 26 | 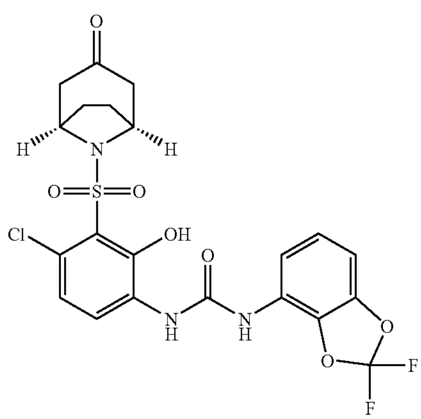 | N-(4-chloro-2-hydroxy-3-{[(1R,5S)-3-oxo-8-azabicyclo[3.2.1]oct-8-yl]sulfonyl}phenyl)-N'-(2,2-difluoro-1,3-benzodioxol-4-yl)urea | Starting material 2, Tropanone, Intermediate 8, (A, G, H) | LCMS (m/z, ES+, M + H): 530.01 |
| 27 | 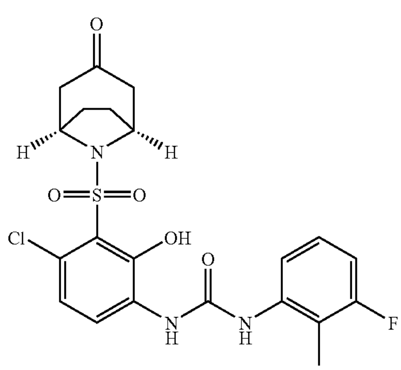 | N-(4-chloro-2-hydroxy-3-{[(1R,5S)-3-oxo-8-azabicyclo[3.2.1]oct-8-yl]sulfonyl}phenyl)-N'-(3-fluoro-2-methylphenyl)urea | Starting material 2, Tropanone, Intermediate 9, (A, G, H) | LCMS (m/z, ES+, M + H): 482.01 |

TABLE 1-continued

Examples prepared according to the general procedures described above

| Ex. | Structure | IUPAC Name | Preparation: Starting materials (General Procedures) | Characterization |
|---|---|---|---|---|
| 28 | 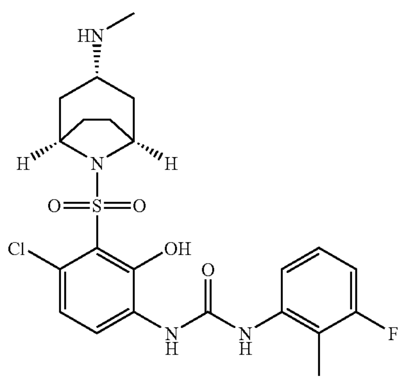 | N-(4-chloro-2-hydroxy-3-{[(1R,5S)-3-(methylamino)-8-azabicyclo[3.2.1]oct-8-yl]sulfonyl}phenyl)-N'-(3-fluoro-2-methylphenyl)urea | Example 27, Methylamine (2M in THF) (F) | LCMS (m/z, ES$^+$, M + H): 497.11 |
| 29 | 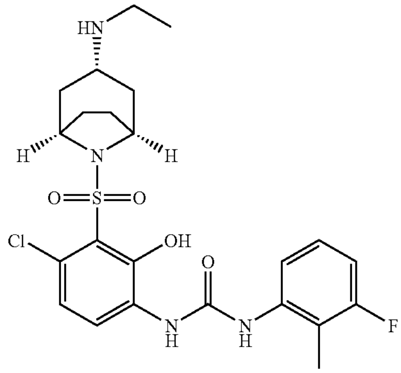 | N-(4-chloro-3-{[(1R,5S)-3-(ethylamino)-8-azabicyclo[3.2.1]oct-8-yl]sulfonyl}-2-hydroxyphenyl)-N'-(3-fluoro-2-methylphenyl)urea | Example 27, Ethylamine (2M in THF) (F) | LCMS (m/z, ES$^+$, M + H): 511.09 |
| 30 | 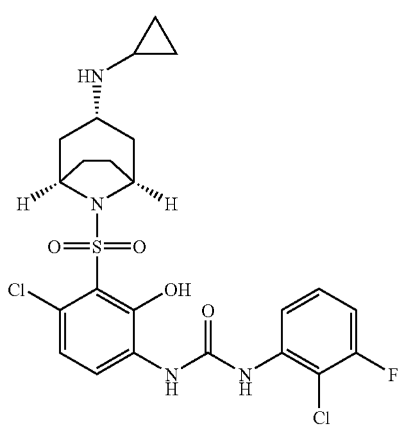 | N-(4-chloro-3-{[(1R,5S)-3-(cyclopropylamino)-8-azabicyclo[3.2.1]oct-8-yl]sulfonyl}-2-hydroxyphenyl)-N'-(2-chloro-3-fluorophenyl)urea | Example 27, cyclopropyl amine, (F) | LCMS (m/z, ES$^+$, M + H): 523.16 |

TABLE 1-continued

Examples prepared according to the general procedures described above

| Ex. | Structure | IUPAC Name | Preparation: Starting materials (General Procedures) | Characterization |
|---|---|---|---|---|
| 31 | 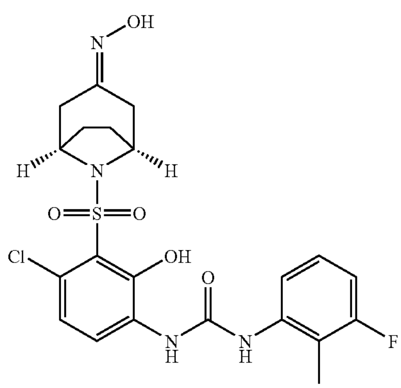 | N-(4-chloro-2-hydroxy-3-{[(1R,5S)-3-(hydroxyimino)-8-azabicyclo[3.2.1]oct-8-yl]sulfonyl}phenyl)-N'-(3-fluoro-2-methylphenyl)urea | Example 27, hydroxylamine, | LCMS (m/z, ES+, M + H): 497.04 |
| 32 | 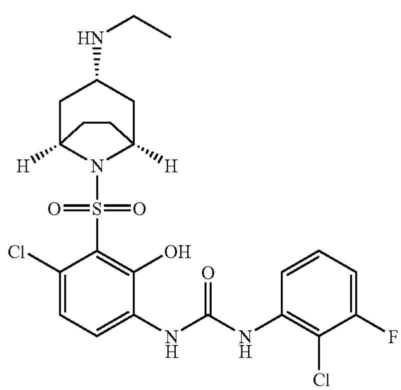 | N-(4-chloro-3-{[(1R,5S)-3-(ethylamino)-8-azabicyclo[3.2.1]oct-8-yl]sulfonyl}-2-hydroxyphenyl)-N'-(2-chloro-3-fluorophenyl)urea | Example 24, Ethylamine (2M in THF) (F) | LCMS (m/z, ES+, M + H): 531.00 |
| 33 | 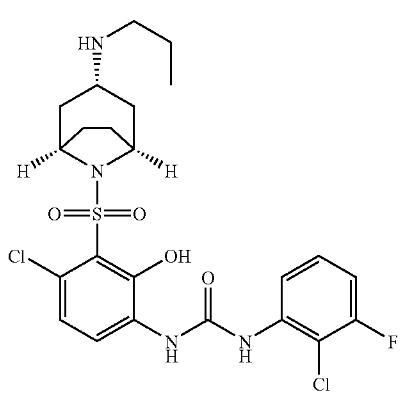 | N-[4-chloro-3-(3,8-diazabicyclo[3.2.1]oct-3-ylsulfonyl)-2-hydroxyphenyl]-N'-[2-(phenyloxy)phenyl]urea | Example 24, propylamine (F) | LCMS (m/z, ES+, M + H): 544.95 |

TABLE 1-continued

Examples prepared according to the general procedures described above

| Ex. | Structure | IUPAC Name | Preparation: Starting materials (General Procedures) | Characterization |
|---|---|---|---|---|
| 34 | 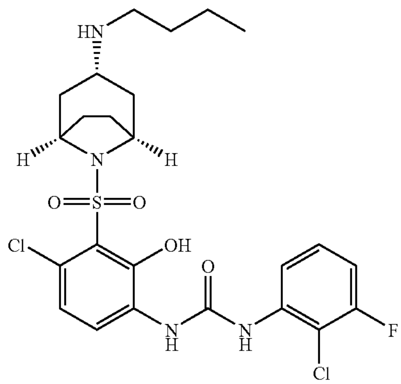 | N-(3-{[(1R,5S)-3-(butylamino)-8-azabicyclo[3.2.1]oct-8-yl]sulfonyl}-4-chloro-2-hydroxyphenyl)-N'-(2-chloro-3-fluorophenyl)urea | Example 24, butylamine (F) | LCMS (m/z, ES+, M + H): 559.01 |
| 35 | 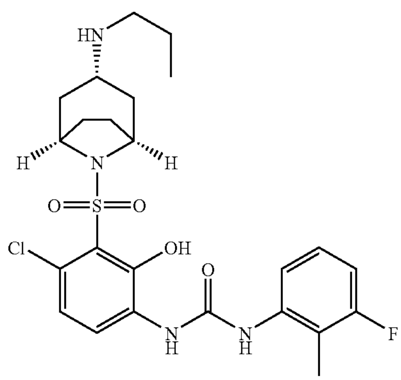 | N-(4-chloro-2-hydroxy-3-{[(1R,5S)-3-(propylamino)-8-azabicyclo[3.2.1]oct-8-yl]sulfonyl}phenyl)-N'-(3-fluoro-2-methylphenyl)urea | Example 27, propylamine (F) | LCMS (m/z, ES+, M + H): 525.15 |
| 36 | 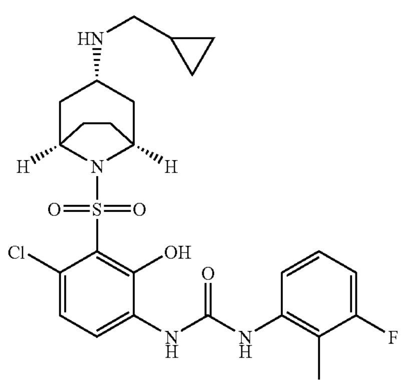 | N-[4-chloro-3-({(1R,5S)-3-[(cyclopropylmethyl)amino]-8-azabicyclo[3.2.1]oct-8-yl}sulfonyl)-2-hydroxyphenyl]-N'-(3-fluoro-2-methylphenyl)urea | Example 27, Cyclopropyl-methylamine, (F) | LCMS (m/z, ES+, M + H): 537.17 |
| 37 | 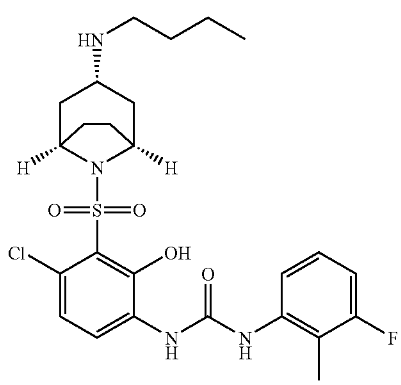 | N-(3-{[(1R,5S)-3-(butylamino)-8-azabicyclo[3.2.1]oct-8-yl]sulfonyl}-4-chloro-2-hydroxyphenyl)-N'-(3-fluoro-2-methylphenyl)urea | Example 24, butylamine (F) | LCMS (m/z, ES+, M + H): 539.20 |

TABLE 1-continued

Examples prepared according to the general procedures described above

| Ex. | Structure | IUPAC Name | Preparation: Starting materials (General Procedures) | Characterization |
|---|---|---|---|---|
| 38 | 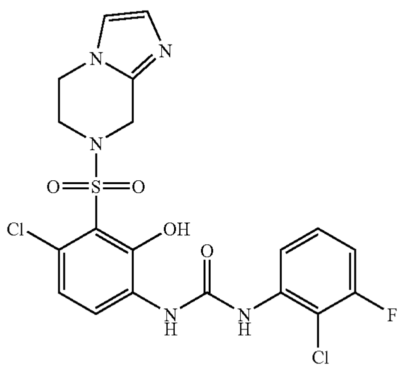 | N-[4-chloro-3-(5,6-dihydroimidazo[1,2-a]pyrazin-7(8H)-ylsulfonyl)-2-hydroxyphenyl]-N'-(2-chloro-3-fluorophenyl)urea | Intermediate 6, 2-chloro-3-fluorophenyl isocyanate, (H) | LCMS (m/z, ES$^+$, M + H): 499.90 |
| 39 | 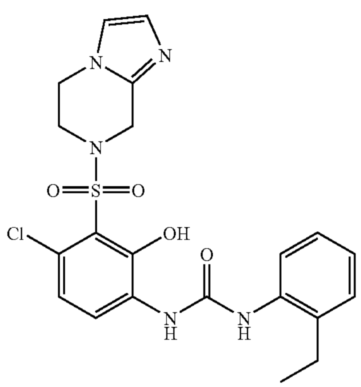 | N-[4-chloro-3-(5,6-dihydroimidazo[1,2-a]pyrazin-7(8H)-ylsulfonyl)-2-hydroxyphenyl]-N'-(2-ethylphenyl)urea | Intermediate 6, 2-ethylphenyl isocyanate, (H) | LCMS (m/z, ES$^+$, M + H): 475.97 |
| 40 | 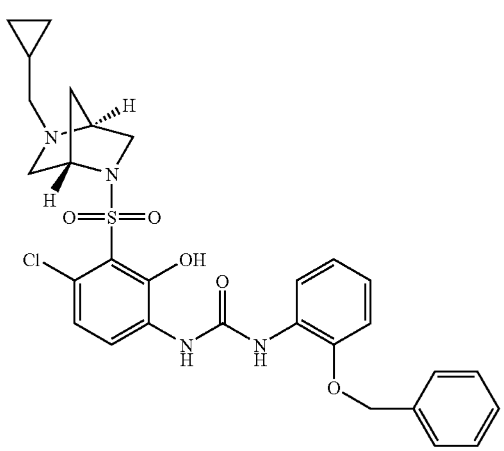 | N-(4-chloro-2-hydroxy-3-{[(1R,5S)-3-oxo-8-azabicyclo[3.2.1]oct-8-yl]sulfonyl}phenyl)-N'-(3-fluoro-2-methylphenyl)urea | Example 6, Cyclopropyl carboxaldehyde (F) | LCMS (m/z, ES$^+$, M + H): 583.13 |

TABLE 1-continued

Examples prepared according to the general procedures described above

| Ex. | Structure | IUPAC Name | Preparation: Starting materials (General Procedures) | Characterization |
|---|---|---|---|---|
| 41 | 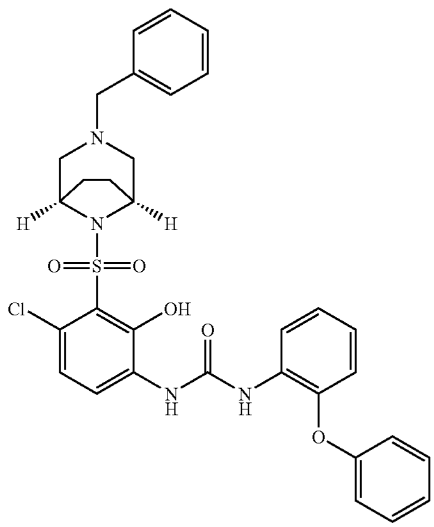 | N-(4-chloro-2-hydroxy-3-{[(1R,5R)-3-(phenylmethyl)-3,8-diazabicyclo[3.2.1]oct-8-yl]sulfonyl}phenyl)-N'-[2-(phenyloxy)phenyl]urea | Intermediate 11, 2-phenoxyphenyl isocyanate, (H) | LCMS (m/z, ES+, M + H): 619.33 |
| 42 | 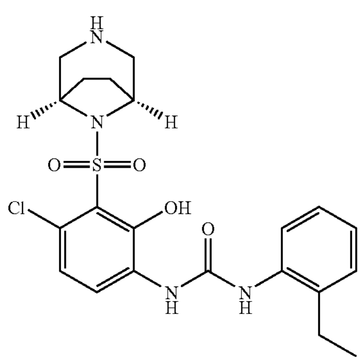 | N-{4-chloro-3-[(1R,5S)-3,8-diazabicyclo[3.2.1]oct-8-ylsulfonyl]-2-hydroxyphenyl}-N'-(2-ethylphenyl)urea | Intermediate 13, 2-ethylphenyl isocyanate (H, E) | LCMS (m/z, ES+, M + H): 465.02 |
| 43 | 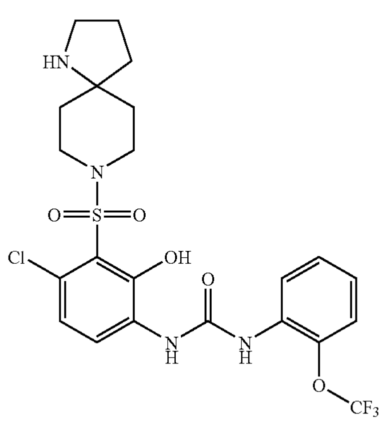 | N-[4-chloro-3-(1,8-diazaspiro[4.5]dec-8-ylsulfonyl)-2-hydroxyphenyl]-N'-{2-[(trifluoromethyl)oxy]phenyl}urea | Starting material 2, 8-Diaza-spiro[4.5]decane-1-carboxylic acid tert-butyl ester, 2-(trifluoromethyloxy)-phenyl isocyanate. (A, B, H, E) | LCMS (m/z, ES+, M + H): 548.98 |

TABLE 1-continued

Examples prepared according to the general procedures described above

| Ex. | Structure | IUPAC Name | Preparation: Starting materials (General Procedures) | Characterization |
|---|---|---|---|---|
| 44 | 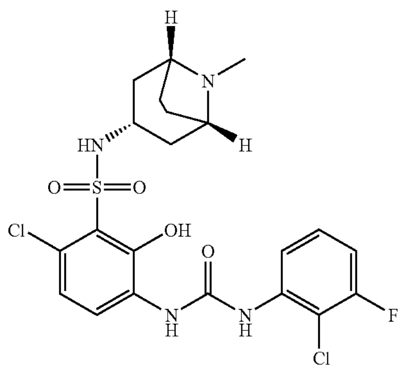 | 6-chloro-3-({[(2-chloro-3-fluorophenyl)amino]carbonyl}amino)-2-hydroxy-N-[(3-endo)-8-methyl-8-azabicyclo[3.2.1]oct-3-yl]benzenesulfonamide | Intermediate 15, Intermediate 3, (D) | LCMS (m/z, ES+, M + H): 516.98 |
| 45 | 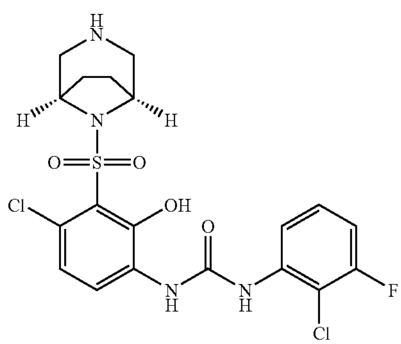 | N-{4-chloro-3-[(1S,5S)-3,8-diazabicyclo[3.2.1]oct-8-ylsulfonyl]-2-hydroxyphenyl}-N'-(2-chloro-3-fluorophenyl)urea | Intermediate 13, 2-ethylphenyl isocyanate, (H, E) | LCMS (m/z, ES+, M + H): 488.95 |
| 46 | 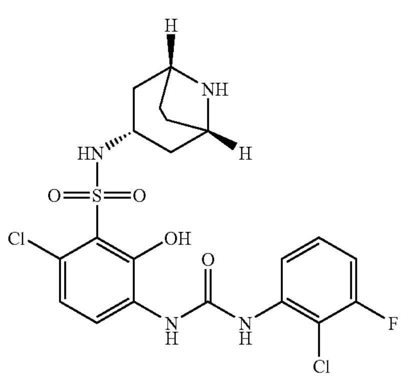 | N-[(1R,5S)-8-azabicyclo[3.2.1]oct-3-yl]-6-chloro-3-({[(2-chloro-3-fluorophenyl)amino]carbonyl}amino)-2-hydroxybenzenesulfonamide | Intermediate 20, (E) | LCMS (m/z, ES+, M + H): 503.08 |

TABLE 1-continued

Examples prepared according to the general procedures described above

| Ex. | Structure | IUPAC Name | Preparation: Starting materials (General Procedures) | Characterization |
|---|---|---|---|---|
| 47 | 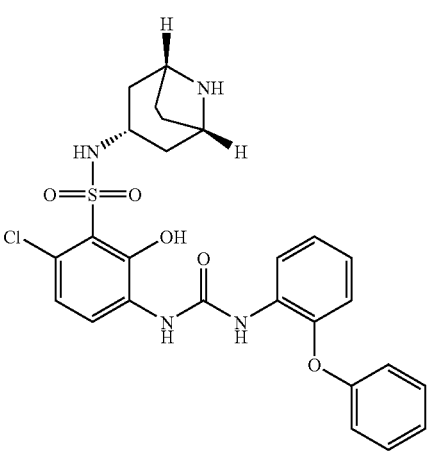 | N-[(1R,5S)-8-azabicyclo[3.2.1]oct-3-yl]-6-chloro-2-hydroxy-3-[({[2-(phenyloxy)phenyl]amino}carbonyl)amino]benzenesulfonamide | Intermediate 19, 2-phenoxyphenyl isocyanate, (H, E) | LCMS (m/z, ES+, M + H): 543.21 |
| 48 | 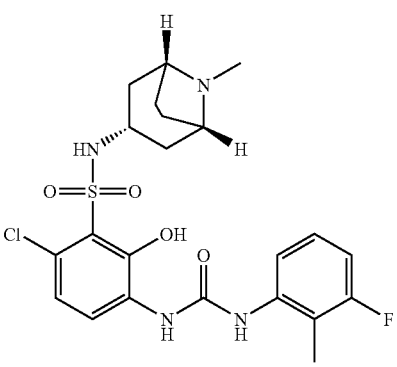 | 6-chloro-3-({[(3-fluoro-2-methylphenyl)amino]carbonyl}amino)-2-hydroxy-N-[(3-endo)-8-methyl-8-azabicyclo[3.2.1]oct-3-yl]benzenesulfonamide | Intermediate 15, Intermediate 9, (H) | LCMS (m/z, ES+, M + H): 497.01 |
| 49 | 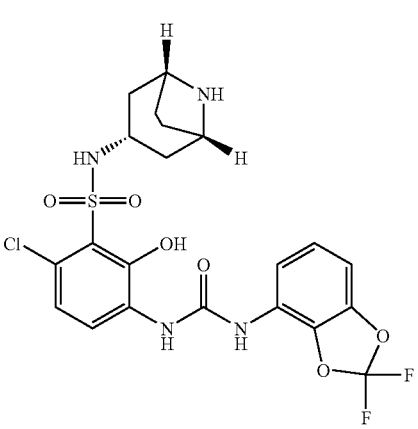 | N-[(3-exo)-8-azabicyclo[3.2.1]oct-3-yl]-6-chloro-3-({[(2,2-difluoro-1,3-benzodioxol-4-yl)amino]carbonyl}amino)-2-hydroxybenzenesulfonamide | Intermediate 19, Intermediate 8, (H, E) | LCMS (m/z, ES+, M + H): 530.96 |

TABLE 1-continued

Examples prepared according to the general procedures described above

| Ex. | Structure | IUPAC Name | Preparation: Starting materials (General Procedures) | Characterization |
|---|---|---|---|---|
| 50 | 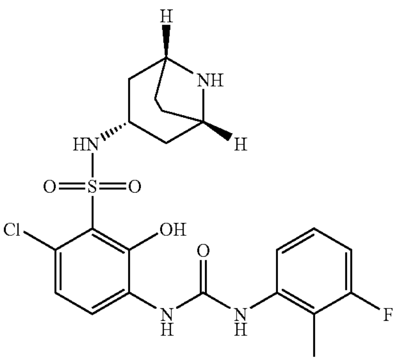 | N-[(1R,5S)-8-azabicyclo[3.2.1]oct-3-yl]-6-chloro-3-({[(3-fluoro-2-methylphenyl)amino]carbonyl}amino)-2-hydroxybenzenesulfonamide | Intermediate 19, Intermediate 9, (H, E) | LCMS (m/z, ES+, M + H): 483.12 |
| 51 | 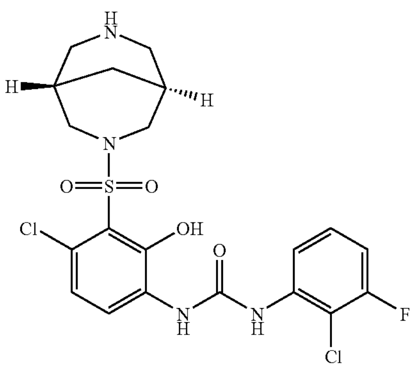 | N-{4-chloro-3-[(1S,5S)-3,7-diazabicyclo[3.3.1]non-3-ylsulfonyl]-2-hydroxyphenyl}-N'-(2-chloro-3-fluorophenyl)urea | Starting material 2, 1,1-dimethylethyl 3,7-diazabicyclo[3.3.1]nonane-3-carboxylate, 2-chloro-3-fluorophenyl isocyanate, (A, J, H, E) | LCMS (m/z, ES+, M + H): 503.02 |
| 52 | 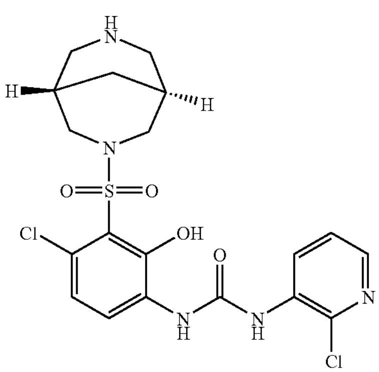 | N-{4-chloro-3-[(1R,5S)-3,7-diazabicyclo[3.3.1]non-3-ylsulfonyl]-2-hydroxyphenyl}-N'-(2-chloro-3-pyridinyl)urea | Starting material 2, 1,1-dimethylethyl 3,7-diazabicyclo[3.2.1]nonane-3-carboxylate, Intermediate 3, (A, J, H, E) | LCMS (m/z, ES+, M + H): 485.96 |
| 53 | 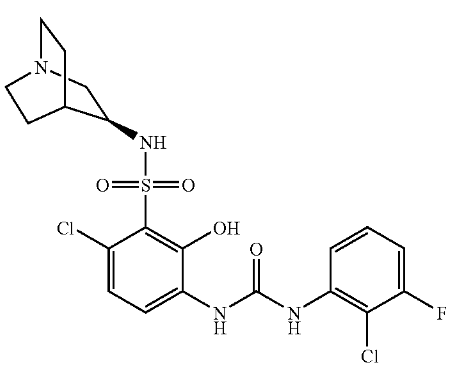 | N-[(3S)-1-azabicyclo[2.2.2]oct-3-yl]-6-chloro-3-({[(2-chloro-3-fluorophenyl)amino]carbonyl}amino)-2-hydroxybenzenesulfonamide | Starting material 2, 3-aminoquinuclidine, Intermediate 3, (A, I, D) | LCMS (m/z, ES+, M + H): 502.95 |

TABLE 1-continued

Examples prepared according to the general procedures described above

| Ex. | Structure | IUPAC Name | Preparation: Starting materials (General Procedures) | Characterization |
|---|---|---|---|---|
| 54 | 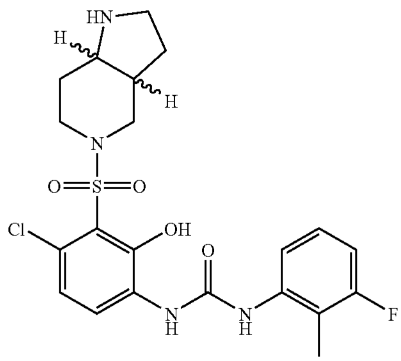 | N-[4-chloro-2-hydroxy-3-(octahydro-5H-pyrrolo[3,2-c]pyridin-5-ylsulfonyl)phenyl]-N'-(3-fluoro-2-methylphenyl)urea | Starting material 2, (+/−)-cis-1,1-dimethylethyl octahydro-1H-pyrrolo[3,2-c]pyridine-1-carboxylate, Intermediate 9, (A, J, H, E) | LCMS (m/z, ES$^+$, M + H): 482.97 |
| 55 | 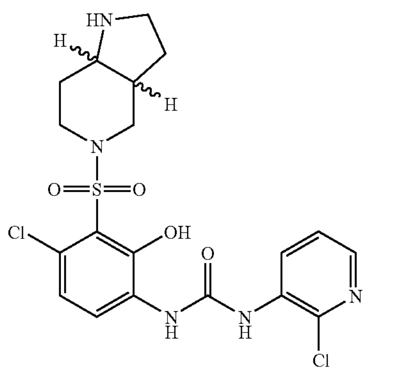 | N-[4-chloro-2-hydroxy-3-(octahydro-5H-pyrrolo[3,2-c]pyridin-5-ylsulfonyl)phenyl]-N'-(2-chloro-3-pyridinyl)urea | Starting material 2, (+/−)-cis-1,1-dimethylethyl octahydro-1H-pyrrolo[3,2-c]pyridine-1-carboxylate, Intermediate 7, (A, J, H, E) | LCMS (m/z, ES$^+$, M + H): 485.96 |
| 56 | 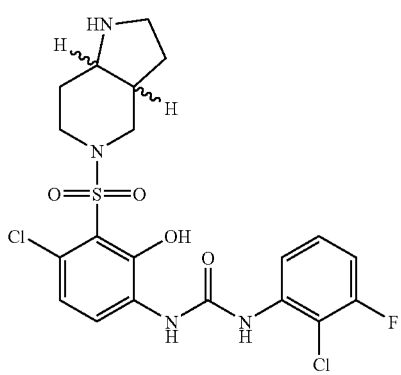 | N-(2-chloro-3-fluorophenyl)-N'-[4-chloro-2-hydroxy-3-(octahydro-5H-pyrrolo[3,2-c]pyridin-5-ylsulfonyl)phenyl]urea | Starting material 2, (+/−)-cis-1,1-dimethylethyl octahydro-1H-pyrrolo[3,2-c]pyridin-1-carboxylate, 2-chloro-3-fluorophenyl isocyanate, (A, J, H, E) | LCMS (m/z, ES$^+$, M + H): 502.89 |

Example 31 was prepared by treating example 27 (435 mg) with hydroxylamine hydrochloride (69 mg) in IMS (5 mL) at reflux for 1 h. Then another 69 mg of hydroxylamine hydrochloride was added and the mixture was refluxed for 1 h, then cooled to room temperature and the solvent was removed in vacuo. EtOAc was added, insoluble material was filtered off and the solvent was evaporated in vacuo yielding 523 mg of product. An aliquot was triturated with EtOAc/Hex to give ~100% pure material (33 mg).

1,1-dimethylethyl 3,7-diazabicyclo[3.3.1]nonane-3-carboxylate was prepared according to WO00/76997, incorporated herein by reference to the extent required to synthesize 1,1-dimethylethyl 3,7-diazabicyclo[3.3.1]nonane-3-carboxylate.

(+/−)-cis-1,1-dimethylethyl octahydro-1H-pyrrolo[3,2-c]pyridine-1-carboxylate was prepared according to *Bioorg. Med. Chem. Lett.* 2005, 15(4), 977, incorporated herein by reference to the extent required to synthesize (+/−)-cis-1,1-dimethylethyl octahydro-1H-pyrrolo[3,2-c]pyridine-1-carboxylate.

Method of Treatment

Compounds of Formula (I), or a pharmaceutically acceptable salt thereof can be used in the manufacture of a medicine for the prophylactic or therapeutic treatment of any disease state in a human, or other mammal, which is exacerbated or caused by excessive or unregulated IL-8 cytokine production by such mammal's cell, such as, but not limited to, monocytes and/or macrophages, or other chemokines which bind to the IL-8 α or β receptor, also referred to as the type I or type II receptor.

Accordingly, the present invention provides a method of treating a chemokine mediated disease, wherein the chemokine is one which binds to an IL-8 α or β receptor and which method comprises administering an effective amount of a compound of Formula (I) or a pharmaceutically acceptable salt thereof. In particular, the chemokines are IL-8, GROα, GROβ, GROγ, NAP-2 or ENA-78.

Compounds of Formula (I) are administered in an amount sufficient to inhibit cytokine function, in particular IL-8, GROα, GROβ, GROγ, NAP-2 or ENA-78, such that they are biologically regulated down to normal levels of physiological function, or in some case to subnormal levels, so as to ameliorate the disease state. Abnormal levels of IL-8, GROα, GROβ, GROγ, NAP-2 or ENA-78, for instance, in the context of the present invention, constitute: (i) levels of free IL-8 greater than or equal to 1 picogram per mL; (ii) any cell associated IL-8, GROα, GROβ, GROγ, NAP-2 or ENA-78 above normal physiological levels; or (iii) the presence of IL-8, GROα, GROβ, GROγ, NAP-2 or ENA-78 above basal levels in cells or tissues in which IL-8, GROα, GROβ, GROγ, NAP-2 or ENA-78 respectively, is produced.

There are many disease states in which excessive or unregulated IL-8 production is implicated in exacerbating and/or causing the disease. Chemokine mediated diseases include psoriasis, atopic dermatitis, osteo arthritis, rheumatoid arthritis, asthma, chronic obstructive pulmonary disease, adult respiratory distress syndrome, inflammatory bowel disease, Crohn's disease, ulcerative colitis, stroke, septic shock, endotoxic shock, gram negative sepsis, toxic shock syndrome, cardiac and renal reperfusion injury, glomerulonephritis, thrombosis, graft vs. host reaction, alzheimers disease, allograft rejections, malaria, restinosis, angiogenesis, atherosclerosis, osteoporosis, gingivitis, viral diseases such as rhinovirus or undesired hematopoietic stem cell release.

These diseases are primarily characterized by massive neutrophil infiltration, T-cell infiltration, or neovascular growth, and are associated with increased IL-8, GROα, GROβ, GROγ, NAP-2 or ENA-78 production which is responsible for the chemotaxis of neutrophils into the inflammatory site or the directional growth of endothelial cells. In contrast to other inflammatory cytokines (IL-1, TNF, and IL-6), IL-8, GROα, GROβ, GROγ, NAP-2 or ENA-78 have the unique property of promoting neutrophil chemotaxis, enzyme release including but not limited to elastase release as well as superoxide production and activation. The α-chemokines, but particularly, GROα, GROβ, GROγ, NAP-2 or ENA-78, working through the IL-8 type I or II receptor, can promote the neovascularization of tumors by promoting the directional growth of endothelial cells. Therefore, the inhibition of IL-8 induced chemotaxis or activation would lead to a direct reduction in the neutrophil infiltration.

Recent evidence also implicates the role of chemokines in the treatment of HIV infections, Littleman et al., *Nature* 381, pp. 661 (1996) and Koup et al., *Nature* 381, pp. 667 (1996).

Present evidence also indicates the use of IL-8 inhibitors in the treatment of atherosclerosis. The first reference, Boisvert et al., *J. Clin. Invest,* 1998, 101:353-363 shows, through bone marrow transplantation, that the absence of IL-8 receptors on stem cells (and, therefore, on monocytes/macrophages) leads to a reduction in the development of atherosclerotic plaques in LDL receptor deficient mice. Additional supporting references are: Apostolopoulos, et al., *Arterioscler. Thromb. Vasc. Biol.* 1996, 16:1007-1012; Liu, et al., *Arterioscler. Thromb. Vasc. Biol,* 1997, 17:317-323; Rus, et al., *Atherosclerosis.* 1996, 127:263-271.; Wang et al., *J. Biol. Chem.* 1996, 271: 8837-8842; Yue, et al., *Eur. J. Pharmacol.* 1993, 240:81-84; Koch, et al.,*Am. J. Pathol.,* 1993, 142:1423-1431.; Lee, et al., *Immunol. Lett.,* 1996, 53, 109-113.; and Terkeltaub et al., *Arterioscler. Thromb.,* 1994, 14:47-53.

The present invention also provides for a means of treating CNS injuries by the chemokine receptor antagonist compounds of Formula (I). Such treatment is provided in an acute setting, as well as for prevention of injury in those individuals deemed susceptible to injury.

CNS injuries as defined herein include both open or penetrating head trauma, such as by surgery, or a closed head trauma injury, such as by an injury to the head region. Also included within this definition is ischemic stroke, particularly to the brain area.

Ischemic stroke may be defined as a focal neurologic disorder that results from insufficient blood supply to a particular brain area, usually as a consequence of an embolus, thrombi, or local atheromatous closure of the blood vessel. The role of inflammatory cytokines in this area has been emerging and the present invention provides means for the potential treatment of these injuries. Relatively little treatment, for an acute injury such as these has been available.

TNF-α is a cytokine with proinflammatory actions, including endothelial leukocyte adhesion molecule expression. Leukocytes infiltrate into ischemic brain lesions and hence compounds which inhibit or decrease levels of TNF would be useful for treatment of ischemic brain injury. See Liu et al., *Stroke,* Vol. 25., No. 7, pp. 1481-88 (1994) whose disclosure is incorporated herein by reference.

Models of closed head injuries and treatment with mixed 5-LO/CO agents is discussed in Shohami et al., *J. of Vaisc & Clinical Physiology and Pharmacology,* Vol. 3, No. 2, pp. 99-107 (1992) whose disclosure is incorporated herein by reference. Treatment which reduced edema formation was found to improve functional outcome in those animals treated.

Compounds of Formula (I) are administered in an amount sufficient to inhibit IL-8, binding to the IL-8 α or β receptors, from binding to these receptors, such as evidenced by a reduction in neutrophil chemotaxis and activation. The discovery that the compounds of Formula (I) are inhibitors of IL-8 binding is based upon the effects of the compounds of Formula (I) in the in vitro receptor binding assays which are described herein. The compounds of Formula (I) have been shown to be inhibitors of type II IL-8 receptors.

As used herein, the term "IL-8 mediated disease or disease state" refers to any and all disease states in which IL-8, GROα, GROβ, GROγ, NAP-2 or ENA-78 plays a role, either by production of IL-8, GROα, GROβ, GROγ, NAP-2 or ENA-78 themselves, or by IL-8, GROα, GROβ, GROγ, NAP-2 or ENA-78 causing another monokine to be released, such as but not limited to IL-1, IL-6 or TNF. A disease state in which, for instance, IL-1 is a major component, and whose production or action, is exacerbated or secreted in response to IL-8, would therefore be considered a disease state mediated by IL-8.

As used herein, the term "chemokine mediated disease or disease state" refers to any and all disease states in which a chemokine which binds to an IL-8 α or β receptor plays a role, such as but not limited to IL-8, GRO-α, GRO-β, GROγ, NAP-2 or ENA-78. This would include a disease state in which IL-8 plays a role, either by production of IL-8 itself, or by IL-8 causing another monokine to be released, such as but not limited to IL-1, IL-6 or TNF. A disease state in which, for instance, IL-1 is a major component, and whose production or action, is exacerbated or secreted in response to IL-8, would therefore be considered a disease stated mediated by IL-8.

As used herein, the term "cytokine" refers to any secreted polypeptide that affects the functions of cells and is a molecule which modulates interactions between cells in the immune, inflammatory or hematopoietic response. A cytokine includes, but is not limited to, monokines and lymphokines, regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epideral keratinocytes and B-lymphocytes. Lymphokines are generally referred to as being produced by lymphocyte cells. Examples of cytokines include, but are not limited to, Interleukin-1 (IL-1), Interleukin-6 (IL-6), Interleukin-8 (IL-8), Tumor Necrosis Factor-alpha (TNF-α) and Tumor Necrosis Factor beta (TNF-β).

As used herein, the term "chemokine" refers to any secreted polypeptide that affects the functions of cells and is a molecule which modulates interactions between cells in the immune, inflammatory or hematopoietic response, similar to the term "cytokine" above. A chemokine is primarily secreted through cell transmembranes and causes chemotaxis and activation of specific white blood cells and leukocytes, neutrophils, monocytes, macrophages, T-cells, B-cells, endothelial cells and smooth muscle cells. Examples of chemokines include, but are not limited to IL-8, GRO-α, GRO-β, GRO-γ, NAP-2, ENA-78, IP-10, MIP-1α, MIP-β, PF4, and MCP 1, 2, and 3.

In order to use a compound of Formula (I) or a pharmaceutically acceptable salt thereof in therapy, it will normally be formulated into a pharmaceutical composition in accordance with standard pharmaceutical practice. This invention, therefore, also relates to a pharmaceutical composition comprising an effective, non-toxic amount of a compound of Formula (I) and a pharmaceutically acceptable carrier or diluent.

Compounds of Formula (I), pharmaceutically acceptable salts thereof and pharmaceutical compositions incorporating such may conveniently be administered by any of the routes conventionally used for drug administration, for instance, orally, topically, parenterally or by inhalation. The compounds of Formula (I) may be administered in conventional dosage forms prepared by combining a compound of Formula (I) with standard pharmaceutical carriers according to conventional procedures. The compounds of Formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl disteatrate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 g. When a liquid carrier is used, the preparation will be in the form of a syrup, emulsion, soft gelatin capsule, sterile injectable liquid such as an ampule or nonaqueous liquid suspension.

Compounds of Formula (I) may be administered topically, that is by non-systemic administration. This includes the application of a compound of Formula (I) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the Formulation. It may however comprise as much as 10% w/w but preferably will comprise less than 5% w/w, more preferably from 0.1% to 1% w/w of the Formulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%)

and chlorhexidine acetate (0.01%). Suitable solvents for the preparation of an oily solution include glycerol, diluted alcohol and propylene glycol.

Compounds of Formula (I) may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. Compounds of Formula (I) may also be administered by inhalation, that is by intranasal and oral inhalation administration. Appropriate dosage forms for such administration, such as an aerosol formulation or a metered dose inhaler, may be prepared by conventional techniques.

For all methods of use disclosed herein for the compounds of Formula (I) the daily oral dosage regimen will preferably be from about 0.01 to about 80 mg/kg of total body weight. The daily parenteral dosage regimen about 0.001 to about 80 mg/kg of total body weight. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of a compound of Formula (I) or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (I) or a pharmaceutically acceptable salt thereof given per day for a defined number of days, can be ascertained by those skilled in the art using conventional course of treatment determination tests.

Combinations:

The compound and pharmaceutical formulations according to the invention may be used in combination with or include one or more other therapeutic agents, for example selected from anti-inflammatory agents, anticholinergic agents (particularly an $M_1/M_2/M_3$ receptor antagonist), β2-adrenoreceptor agonists, antiinfective agents, such as antibiotics, antivirals, or antihistamines. The invention thus provides, in a further aspect, a combination comprising a compound of Formula (I) or a pharmaceutically acceptable salt, solvate or physiologically functional derivative thereof together with one or more other therapeutically active agents, for example selected from an anti-inflammatory agent, such as a corticosteroid or an NSAID, an anticholinergic agent, a $β_2$-adrenoreceptor agonist, an antiinfective agent, such as an antibiotic or an antiviral, or an antihistamine. One embodiment of the invention encompasses combinations comprising a compound of Formula (I) or a pharmaceutically acceptable salt, solvate or physiologically functional derivative thereof together with a $β_2$-adrenoreceptor agonist, and/or an anticholinergic, and/or a PDE-4 inhibitor, and/or an antihistamine.

One embodiment of the invention encompasses combinations comprising one or two other therapeutic agents.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates to optimise the activity and/or stability and/or physical characteristics, such as solubility, of the therapeutic ingredient. It will be clear also that, where appropriate, the therapeutic ingredients may be used in optically pure form.

In one embodiment, the invention encompasses a combination comprising a compound of the invention together with a $β_2$-adrenoreceptor agonist.

Examples of $β_2$-adrenoreceptor agonists include salmeterol (which may be a racemate or a single enantiomer such as the R-enantiomer), salbutamol (which may be a racemate or a single enantiomer such as the R-enantiomer), formoterol (which may be a racemate or a single diastereomer such as the R,R-diastereomer), salmefamol, fenoterol, carmoterol, etanterol, naminterol, clenbuterol, pirbuterol, flerbuterol, reproterol, bambuterol, indacaterol, terbutaline and salts thereof, for example the xinafoate (1-hydroxy-2-naphthalenecarboxylate) salt of salmeterol, the sulphate salt or free base of salbutamol or the fumarate salt of formoterol. In one embodiment the $β_2$-adrenoreceptor agonists are long-acting $β_2$-adrenoreceptor agonists, for example, compounds which provide effective bronchodilation for about 12 hours or longer. Other $β_2$-adrenoreceptor agonists include those described in WO2002/066422, WO2002/070490, WO2002/076933, WO2003/024439, WO2003/072539, WO2003/091204, WO2004/016578, WO2004/022547, WO2004/037807, WO2004/037773, WO2004/037768, WO2004/039762, WO2004/039766, WO2001/42193 and WO2003/042160.

Further examples of $β_2$-adrenoreceptor agonists include:

3-(4-{[6-({(2R)-2-hydroxy-2-[4-hydroxy-3-(hydroxymethyl)phenyl]ethyl}amino)hexyl]oxy}butyl)benzenesulfonamide;

3-(3-{[7-({(2R)-2-hydroxy-2-[4-hydroxy-3-hydroxymethyl)phenyl]ethyl}-amino) heptyl]oxy}propyl)benzenesulfonamide;

4-{(1R)-2-[(6-{2-[(2,6-dichlorobenzyl) oxy]ethoxy}hexyl) amino]-1-hydroxyethyl}-2-(hydroxymethyl)phenol;

4-{(1R)-2-[(6-{4-[3-(cyclopentylsulfonyl)phenyl] butoxy}hexyl)amino]-1-hydroxyethyl}-2-(hydroxymethyl)phenol;

N-[2-hydroxyl-5-[(1R)-1-hydroxy-2-[[2-4-[[(2R)-2-hydroxy-2-phenylethyl]amino]phenyl]ethyl]amino]ethyl] phenyl]formamide;

N-2 {2-[4-(3-phenyl-4-methoxyphenyl)aminophenyl] ethyl}-2-hydroxy-2-(8-hydroxy-2(1H)-quinolinon-5-yl) ethylamine; and 5-[(R)-2-(2-{4-[4-(2-amino-2-methyl-propoxy)-phenylamino]-phenyl}-ethylamino)-1-hydroxyethyl]-8-hydroxy-1H-quinolin-2-one.

The $β_2$-adrenoreceptor agonist may be in the form of a salt formed with a pharmaceutically acceptable acid selected from sulphuric, hydrochloric, fumaric, hydroxynaphthoic (for example 1- or 3-hydroxy-2-naphthoic), cinnamic, substituted cinnamic, triphenylacetic, sulphamic, sulphanilic, naphthaleneacrylic, benzoic, 4-methoxybenzoic, 2- or 4-hydroxybenzoic, 4-chlorobenzoic and 4-phenylbenzoic acid.

Suitable anti-inflammatory agents include corticosteroids. Examples of corticosteroids which may be used in combination with the compounds of the invention are those oral and inhaled corticosteroids and their pro-drugs which have anti-inflammatory activity.

Examples include methyl prednisolone, prednisolone, dexamethasone, fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate), 6α,9α-difluoro-11β-hydroxy-16α-methyl-3-oxo- 17α-propionyloxy-androsta-1,4-diene-17β-carbothioic acid S-(2-oxo-tetrahydro-furan-3 S-yl) ester, 6α,9α-difluoro-11β-hydroxy-16α-methyl-3-oxo-17α-(2,2,3,3-tetramethylcyclopropylcarbonyl)oxy-androsta-1,4-diene-17β-carbothioic acid S-cyanomethyl ester and 6α,9α-difluoro-11β-hydroxy-16α-methyl-17α-(1-methylcyclopropylcarbonyl)oxy-3-oxo-androsta-1,4-diene-17β-carbothioic acid S-fluoromethyl ester, beclomethasone esters (for example the 17-propionate ester or the 17,21-dipropionate ester), budesonide, flunisolide, mometasone esters (for example mometasone furoate), triamcinolone acetonide, rofleponide, ciclesonide (16α,17-[[(R)-cyclohexylmethylene]bis(oxy)]-11β,21-dihydroxy-pregna-1,4-diene-3,20-dione), butixocort propionate, RPR-106541, and ST-126. In one embodiment corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-(2,2,3,3-tetramethycyclopropylcarbonyl)oxy-androsta-1,4-diene-17β-carbothioic acid S-cyanomethyl ester and 6α,9α-difluoro-11β-hydroxy-16α-methyl-17α-(1-methycyclopropylcarbonyl)oxy-3-oxo-androsta-1,4-diene-17β-carbothioic acid S-fluoromethyl ester. In one embodiment the corticosteroid is 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

Examples of corticosteroids also include those described in WO2002/088167, WO2002/100879, WO2002/12265, WO2002/12266, WO2005/005451, WO2005/005452, WO2006/072599 and WO2006/072600.

Non-steroidal compounds having glucocorticoid agonism that may possess selectivity for transrepression over transactivation and that may be useful in combination therapy include those covered in the following published patent applications and patents: WO2003/082827, WO1998/54159, WO2004/005229, WO2004/009017, WO2004/018429, WO2003/104195, WO2003/082787, WO2003/082280, WO2003/059899, WO2003/101932, WO2002/02565, WO2001/16128, WO2000/66590, WO2003/086294, WO2004/026248, WO2003/061651, WO2003/08277, WO2006/000401, WO2006/000398 and WO2006/015870.

Non-steroidal compounds having glucocorticoid agonism that may possess selectivity for transrepression over transactivation and that may be useful in combination therapy include those covered in the following patents: WO2003/082827, WO1998/54159, WO2004/005229, WO2004/009017, WO2004/018429, WO2003/104195, WO2003/082787, WO2003/082280, WO2003/059899, WO2003/101932, WO2002/02565, WO2001/16128, WO2000/66590, WO2003/086294, WO2004/026248, WO2003/061651 and WO2003/08277.

Examples of anti-inflammatory agents include non-steroidal anti-inflammatory drugs (SAID's).

Examples of NSAID's include sodium cromoglycate, nedocromil sodium, phosphodiesterase (PDE) inhibitors (for example, theophylline, PDE4 inhibitors or mixed PDE3/PDE4 inhibitors), leukotriene antagonists, inhibitors of leukotriene synthesis (for example montelukast), iNOS inhibitors, tryptase and elastase inhibitors, beta-2 integrin antagonists and adenosine receptor agonists or antagonists (e.g. adenosine 2a agonists), cytokine antagonists (for example chemokine antagonists, such as a CCR3 antagonist) or inhibitors of cytokine synthesis, or 5-lipoxygenase inhibitors. In one embodiment, the invention encompasses iNOS (inducible nitric oxide synthase) inhibitors for oral administration. Examples of iNOS inhibitors include those disclosed in WO1993/13055, WO1998/30537, WO2002/50021, WO1995/34534 and WO1999/62875. Examples of CCR3 inhibitors include those disclosed in WO2002/26722.

In one embodiment the invention provides the use of the compounds of Formula (I) in combination with a phosphodiesterase 4 (PDE4) inhibitor, for example in the case of a formulation adapted for inhalation. The PDE4 inhibitor useful in this aspect of the invention may be any compound that is known to or which is discovered to act as a PDE4 inhibitor, e.g. as an inhibitor of PDE4B and/or PDE4D.

PDE4 inhibitory compounds include cis-4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl)cyclohexan-1-ol]. Also, cis-4-cyano-4-[3-(cyclopentyloxy)-4-methoxyphenyl]cyclohexane-1-carboxylic acid (also known as cilomilast) and its salts, esters, pro-drugs or physical forms, which is described in U.S. Pat. No. 5,552,438 issued 3 Sep. 1996; this patent and the compounds it discloses are incorporated herein in full by reference.

Other PDE4 inhibitory compounds include AWD-12-281 (N-(3,5-dichloro-4-pyridinyl)-1-[4-fluorophenyl)methyl]-5-hydroxy-α-oxo-1H-indol-3-acetamide) from Elbion (Hofgen, N. et al. 15th EFMC Int Symp Med Chem (September 6-10, Edinburgh) 1998, Abst P.98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (September 19-23, Geneva) 1998] 1998, 12 (Suppl. 28): Abst P2393); roflumilast (3-(cyclopropylmethoxy)-N-(3,5-dichloro-4-pyridinyl)-4-(difluoromethoxy)benzamide) (see EP 0 706 513 B1 to Byk Gulden Lomberg, e.g. see Example 5 thereof); a phthalazinone (WO 1999/47505) from Byk-Gulden; Pumafentrine, (−)-p-[(4aR*,10bS*)-9-ethoxy-1,2,3,4,4a,10b-hexahydro-8-methoxy-2-methylbenzo[c][1,6]naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al. J Pharmacol Exp Ther, 1998, 284(1): 162), and T2585.

Further PDE4 inhibitory compounds are disclosed in the published international patent applications WO2004/024728, WO2004/056823, WO2004/103998 (e.g. Example 399 or 544 disclosed therein), WO2005/058892, WO2005/090348, WO2005/090353, and WO2005/090354, all in the name of Glaxo Group Limited.

Examples of anticholinergic agents are those compounds that act as antagonists at the muscarinic receptors, in particular those compounds which are antagonists of the $M_1$ or $M_3$ receptors, dual antagonists of the $M_1/M_3$ or $M_2/M_3$, receptors or pan-antagonists of the $M_1/M_2/M_3$ receptors. Exemplary compounds for administration via inhalation include ipratropium (for example, as the bromide, CAS 22254-24-6, sold under the name Atrovent), oxitropium (for example, as the bromide, CAS 30286-75-0) and tiotropium (for example, as the bromide, CAS 136310-93-5, sold under the name Spiriva). Also of interest are revatropate (for example, as the hydrobromide, CAS 262586-79-8) and LAS-34273 which is disclosed in WO2001/04118. Exemplary compounds for oral administration include pirenzepine (CAS 28797-61-7), darifenacin (CAS 133099-04-4, or CAS 133099-07-7 for the hydrobromide sold under the name Enablex), oxybutynin (CAS 5633-20-5, sold under the name Ditropan), terodiline (CAS 15793-40-5), tolterodine (CAS 124937-51-5, or CAS 124937-52-6 for the tartrate, sold under the name Detrol), otilonium (for example, as the bromide, CAS 26095-59-0, sold under the name Spasmomen), trospium chloride (CAS 10405-02-4) and solifenacin (CAS 242478-37-1, or CAS 242478-38-2 for the succinate also known as YM-905 and sold under the name Vesicare).

Additional compounds are disclosed in WO 2005/037280, WO 2005/046586 and WO 2005/104745, incorporated herein by reference. The present combinations include, but are not limited to:

(3-endo)-3-(2,2-di-2-thienylethenyl)-8,8-dimethyl-8-azoniabicyclo[3.2.1]octane iodide;

(3-endo)-3-(2-cyano-2,2-diphenylethyl)-8,8-dimethyl-8-azoniabicyclo[3.2.1]octane bromide;

4-[hydroxy(diphenyl)methyl]-1-{2-[(phenylmethyl)oxy]ethyl}-1-azoniabicyclo[2.2.2]octane bromide; and (1R,5S)-3-(2-cyano-2,2-diphenylethyl)-8-methyl-8-{2-[(phenylmethyl)oxy]ethyl}-8-azoniabicyclo[3.2.1]octane bromide.

Other anticholinergic agents include compounds which are disclosed in U.S. patent application 60/487,981, incorporated herein in its entirety by reference. These include, for example:

(endo)-3-(2-methoxy-2,2-di-thiophen-2-yl-ethyl)-8,8-dimethyl-8-azonia-bicyclo[3.2.1]octane iodide;

3-((endo)-8-methyl-8-aza-bicyclo[3.2.1]oct-3-yl)-2,2-diphenyl-propionitrile;

(endo)-8-methyl-3-(2,2,2-triphenyl-ethyl)-8-aza-bicyclo[3.2.1]octane;

3-((endo)-8-methyl-8-aza-bicyclo[3.2.1]oct-3-yl)-2,2-diphenyl-propionamide;

3-((endo)-8-methyl-8-aza-bicyclo[3.2.1]oct-3-yl)-2,2-diphenyl-propionic acid;

(endo)-3-(2-cyano-2,2-diphenyl-ethyl)-8,8-dimethyl-8-azonia-bicyclo[3.2.1]octane iodide;

(endo)-3-(2-cyano-2,2-diphenyl-ethyl)-8,8-dimethyl-8-azonia-bicyclo[3.2.1]octane bromide;

3-((endo)-8-methyl-8-aza-bicyclo[3.2.1]oct-3-yl)-2,2-diphenyl-propan-1-ol;

N-benzyl-3-((endo)-8-methyl-8-aza-bicyclo[3.2.1]oct-3-yl)-2,2-diphenyl-propionamide;

(endo)-3-(2-carbamoyl-2,2-diphenyl-ethyl)-8,8-dimethyl-8-azonia-bicyclo[3.2.1]octane iodide;

1-benzyl-3-[3-((endo)-8-methyl-8-aza-bicyclo[3.2.1]oct-3-yl)-2,2-diphenyl-propyl]-urea;

1-ethyl-3-[3-((endo)-8-methyl-8-aza-bicyclo[3.2.1]oct-3-yl)-2,2-diphenyl-propyl]-urea;

N-[3-((endo)-8-methyl-8-aza-bicyclo[3.2.1]oct-3-yl)-2,2-diphenyl-propyl]-acetamide;

N-[3-((endo)-8-methyl-8-aza-bicyclo[3.2.1]oct-3-yl)-2,2-diphenyl-propyl]-benzamide;

3-((endo)-8-methyl-8-aza-bicyclo[3.2.1]oct-3-yl)-2,2-di-thiophen-2-yl-propionitrile;

(endo)-3-(2-cyano-2,2-di-thiophen-2-yl-ethyl)-8,8-dimethyl-8-azonia-bicyclo[3.2.1]octane iodide;

N-[3-((endo)-8-methyl-8-aza-bicyclo[3.2.1]oct-3-yl)-2,2-diphenyl-propyl]-benzenesulfonamide;

[3-((endo)-8-methyl-8-aza-bicyclo[3.2.1]oct-3-yl)-2,2-diphenyl-propyl]-urea;

N-[3-((endo)-8-methyl-8-aza-bicyclo[3.2.1]oct-3-yl)-2,2-diphenyl-propyl]-methanesulfonamide; and/or (endo)-3-{2,2-diphenyl-3-[(1-phenyl-methanoyl)-amino]-propyl}-8,8-dimethyl-8-azonia-bicyclo[3.2.1]octane bromide.

Further compounds include:

(endo)-3-(2-methoxy-2,2-di-thiophen-2-yl-ethyl)-8,8-dimethyl-8-azonia-bicyclo[3.2.1]octane iodide;

(endo)-3-(2-cyano-2,2-diphenyl-ethyl)-8,8-dimethyl-8-azonia-bicyclo[3.2.1]octane iodide;

(endo)-3-(2-cyano-2,2-diphenyl-ethyl)-8,8-dimethyl-8-azonia-bicyclo[3.2.1]octane bromide;

(endo)-3-(2-carbamoyl-2,2-diphenyl-ethyl)-8,8-dimethyl-8-azonia-bicyclo[3.2.1]octane iodide;

(endo)-3-(2-cyano-2,2-di-thiophen-2-yl-ethyl)-8,8-dimethyl-8-azonia-bicyclo[3.2.1]octane iodide; and/or (endo)-3-{2,2-diphenyl-3-[(1-phenyl-methanoyl)-amino]-propyl}-8,8-dimethyl-8-azonia-bicyclo[3.2.1]octane bromide.

In one embodiment the invention provides a combination comprising a compound of Formula (I) or a pharmaceutically acceptable salt thereof together with an H1 antagonist. Examples of H1 antagonists include, without limitation, amelexanox, astemizole, azatadine, azelastine, acrivastine, brompheniramine, cetirizine, levocetirizine, efletirizine, chlorpheniramine, clemastine, cyclizine, carebastine, cyproheptadine, carbinoxamine, descarboethoxyloratadine, doxylamine, dimethindene, ebastine, epinastine, efletirizine, fexofenadine, hydroxyzine, ketotifen, loratadine, levocabastine, mizolastine, mequitazine, mianserin, noberastine, meclizine, norastemizole, olopatadine, picumast, pyrilamine, promethazine, terfenadine, tripelennamine, temelastine, trimeprazine and triprolidine, particularly cetirizine, levocetirizine, efletirizine and fexofenadine. In a further embodiment the invention provides a combination comprising a compound of Formula (I), or a pharmaceutically acceptable salt thereof together with an H3 antagonist (and/or inverse agonist). Examples of H3 antagonists include, for example, those compounds disclosed in WO2004/035556 and in WO2006/045416. Other histamine receptor antagonists which may be used in combination with the compounds of the present invention include antagonists (and/or inverse agonists) of the H4 receptor, for example, the compounds disclosed in Jablonowski et al., J. Med. Chem. 46:3957-3960 (2003).

In one embodiment, the invention provides a combination comprising a compound of Formula (I) or a pharmaceutically acceptable salt thereof together with a CCR5 receptor antagonist, such as 4,4-difluoro-N-((1S)-3-{3-[3-methyl-5-(1-methylethyl)-4H-1,2,4-triazol-4-yl]-8-azabicyclo[3.2.1]oct-8-yl}-1-phenylpropyl)cyclohexanecarboxamide:

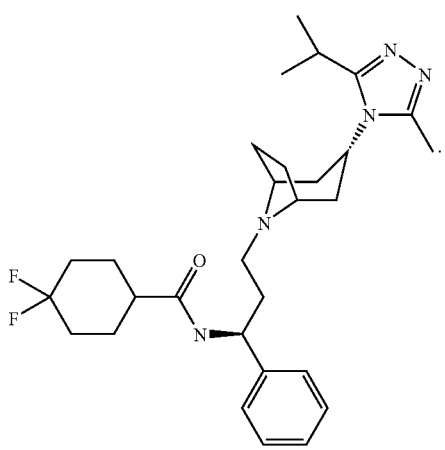

In one embodiment, the invention provides a combination comprising a compound of Formula (I) or a pharmaceutically acceptable salt thereof together with a CXCR3 receptor antagonist such as N-((1R)-1-{3-[4-(ethyloxy)phenyl]-4-oxo-3,4-dihydropyrido[2,3-d]pyrimidin-2-yl}ethyl)-N-(3-pyridinylmethyl)-2-{4-[(trifluoromethyl)oxy]phenyl}acetamide:

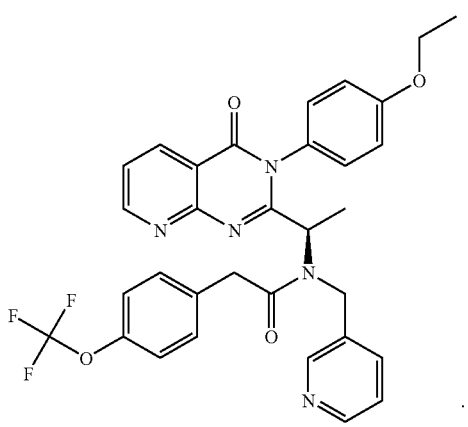

The invention thus provides, in a further aspect, a combination comprising a compound of Formula (I) and/or a pharmaceutically acceptable salt, solvate or physiologically functional derivative thereof together with a PDE4 inhibitor.

The invention thus provides, in a further aspect, a combination comprising a compound of Formula (I) and/or a pharmaceutically acceptable salt, solvate or physiologically functional derivative thereof together with a $\beta_2$-adrenoreceptor agonist.

The invention thus provides, in a further aspect, a combination comprising a compound of Formula (I) and/or a pharmaceutically acceptable salt, solvate or physiologically functional derivative thereof together with a corticosteroid.

The invention thus provides, in a further aspect, a combination comprising a compound of Formula (I) and/or a pharmaceutically acceptable salt, solvate or physiologically functional derivative thereof together with a non-steroidal GR agonist.

The invention thus provides, in a further aspect, a combination comprising a compound of Formula (I) and/or a pharmaceutically acceptable salt, solvate or physiologically functional derivative thereof together with an anticholinergic.

The invention thus provides, in a further aspect, a combination comprising a compound of Formula (I) and/or a pharmaceutically acceptable salt, solvate or physiologically functional derivative thereof together with an antihistamine.

The invention thus provides, in a further aspect, a combination comprising a compound of Formula (I) and/or a pharmaceutically acceptable salt, solvate or physiologically functional derivative thereof together with a PDE4 inhibitor and a $\beta_2$-adrenoreceptor agonist.

The invention thus provides, in a further aspect, a combination comprising a compound of Formula (I) and/or a pharmaceutically acceptable salt, solvate or physiologically functional derivative thereof together with an anticholinergic and a PDE-4 inhibitor.

The combinations referred to above may conveniently be presented for use in the form of a pharmaceutical formulation and thus pharmaceutical formulations comprising a combination as defined above together with a pharmaceutically acceptable diluent or carrier represent a further aspect of the invention.

The individual compounds of such combinations may be administered either sequentially or simultaneously in separate or combined pharmaceutical formulations. In one embodiment, the individual compounds will be administered simultaneously in a combined pharmaceutical formulation. Appropriate doses of known therapeutic agents will readily be appreciated by those skilled in the art.

The invention thus provides, in a further aspect, a pharmaceutical composition comprising a combination of a compound of the invention together with another therapeutically active agent.

The invention thus provides, in a further aspect, a pharmaceutical composition comprising a combination of a compound of the invention together with a PDE4 inhibitor.

The invention thus provides, in a further aspect, a pharmaceutical composition comprising a combination of a compound of the invention together with a $\beta_2$-adrenoreceptor agonist.

The invention thus provides, in a further aspect, a pharmaceutical composition comprising a combination of a compound of the invention together with a corticosteroid.

The invention thus provides, in a further aspect, a pharmaceutical composition comprising a combination of a compound of the invention together with a non-steroidal GR agonist.

The invention thus provides, in a further aspect, a pharmaceutical composition comprising a combination of a compound of the invention together with an anticholinergic.

The invention thus provides, in a further aspect, a pharmaceutical composition comprising a combination of a compound of the invention together with an antihistamine.

The invention thus provides, in a further aspect, a pharmaceutical composition comprising a combination of a compound of the invention together with CXCR3 receptor antagonist.

The invention thus provides, in a further aspect, a pharmaceutical combination of the invention together with a CCR5 receptor antagonist.

The invention will now be described by reference to the following biological examples which are merely illustrative and are not to be construed as a limitation of the scope of the present invention.

BIOLOGICAL EXAMPLES

The IL-8, and GRO-α chemokine inhibitory effects of compounds of the present invention are determined by the following assays:

Receptor Binding Assays:

[$^{125}$I] IL-8 (human recombinant) was obtained from GE Healthcare, with specific activity 2000 Ci/mmol. All other chemicals were of analytical grade. High levels of recombinant human CXCR1 (IL-8 type α) and CXCR2 (IL-8 type β) receptors were individually expressed in non-adherent Chinese Hamster Ovary (CHO) cells as described previously (Holmes, et at., *Science*, 1991, 253, 1278). The membranes were prepared according to a previously described protocol, Haour, et al., *J. Biol. Chem.*, 249 pp 2195-2205 (1974)), except that the homogenization buffer was modified to 40 mM Tris-HCL (pH 7.5), 1 mM $MgSO_4$, 0.5 mM EGTA (ethylene-glycol-bis(2-aminoethylether)-N,N,N',N' tetra-acetic acid), 1 mM PMSF α-toluenesulphonyl fluoride), 2.5 mg/L leupeptin and 0.1 mg/ml aprotinin. Cells were homogenized and centrifuged at 2,000 rpm for 10 min. The supernatant was centrifuged at 100,000×g for 1 hour. Supernatant discarded and membranes stored at −80° C. Membrane protein concentration was determined using BioRad reagent according to manufactures protocol using bovine serum albumin (BSA) as a standard.

All IL-8 binding was conducted using Scintillation Proximity Assays (SPA) using wheatgerm agglutinin beads in a 96-well plate format. Membranes CHO—CXCR1 or CHO—CXCR2 were preincubated with the beads in the binding buffer for 30 min. for 4° C. Buffer contained 20 mM Bis-Trispropane buffer, pH 8.0, containing 1 mM $MgSO_4$, 0.1 mM EDTA and 25 mM NaCl. Compounds were diluted in DMSO at 20× the final dilution (final compound concentration between 1 nM and 30 uM and final DMSO concentration of 5%). Assay was performed in 96-well plates (optiplate 96, Packard) at room temperature, in 0.1 ml binding buffer with membranes and 0.04% CHAPS (3-[(3-cholamidopropyl) dimethylammonio]-1-propanesulfonate), 0.0025% BSA and 0.23 nM [$^{125}$I] IL-8. Plates were shaken on a platform for 1 hour, at the end of incubation the plates were spun at 2,000 rpm for 5 min and counted in a Top Count counter The recombinant IL-8 Rα, CXCR1 or Type I, receptor is also referred to herein as the non-permissive receptor and the recombinant IL-8 Rβ, CXCR2 or Type TI, receptor is referred to as the permissive receptor.

Exemplified compounds of Formula (I), Examples 1 through 53, exhibited positive inhibitory activity in this assay at $IC_{50}$ levels <30 uM, and would be considered active.

CD11b Human Whole Blood Assay:

The compounds indicated were tested for their ability to inhibit the GROα-induced expression of the integrin CD11b on neutrophils in human whole blood.

Blood was drawn (9 ml) using a butterfly line and a 10 ml syringe containing 0.2 ml of working Sodium Heparin. The blood was kept at 37° C. until placed on ice in step 5 below. Compound stock solutions were then diluted to 12 times the maximum final concentration, 120 uM. Half Log serial dilutions were then performed in vehicle. Ten microliters of the compound dilutions or vehicle were then added to the appropriate 12×75 polypropylene tubes. One hundred microliters of whole blood was added per tube and incubated for 10 minutes, in a 37° C. water bath with initial (gentle) agitation and again at 5 minutes. The GROα stock was diluted 1:166.66 in 0.1% BSA-DPBS to "12×" concentration of 120 nM and 10 ul of the GROα dilution or 01% BSA-DPBS was added to the appropriate tubes so that the final GROα concentration equaled 10 nM. The tubes were incubated for 10 min at 37° C. with gentle hand agitation and again at 5 minutes. Samples were then placed on ice and 250 ul of ice cold CellFix working dilution was added followed by a one minute incubation on ice. 1.5 ml Eppendorf tubes were readied during GROα incubation by adding the appropriate antibodies. Every tube received 10 ul of CD11b-FITC and 5 ul of CD16-PE, except for the isotype control which received 10 ul of IgG2a-FITC instead of CD11b. Addition of 50 ul of the fixed blood from each tube was added to the appropriate Eppendorf tube. Samples were allowed to then incubate for 20 min at 4° C. in the dark. Addition of the blood/antibody mixtures to 500 ul of cold DPBS were added to the appropriately labeled 12×75 polystyrene tube. The resulting mixture was kept on ice. LDS stock (10 ul) was added and the mixture was incubated for 10 min at 4° C. before flow analysis. Samples were kept in a darkened environment. The LDS addition was staggered as the samples were collected on the flow cytometer so that all samples were run ~10-20 minutes post-LDS addition.

Medium flow rate was used for flow collection and FL3 threshold increased to eliminate red blood cells from analysis using the LDS signal. The color compensation was properly set using unlabeled samples and one-color samples to subtract LDS spill into PE and the PE spill into FITC and FITC into PE. For the BD LSR cytometer, LDS=FL3, PE=FL2, FITC=FL1. A minimum of 2000-3000 events that satisfy the granulocyte gate by SSC vs. FSC and were CD16 positive by the FL2 signal were collected.

Exemplified compounds of Formula (I), Examples 1-3, 12, 17, 18, 23, 26 and 45 exhibited positive inhibitory activity in this assay at $IC_{50}$ values of <5 uM, and would be considered active. Compounds of Examples 1-3, 12, 17, 18, 23, 26 and 45, tested by the above assay had an $IC_{50}$ from about 3 uM to about 0.7 uM.

Calcium Mobilization in CHO-K1 Cells Stably Expressing CXCR2 and Gα16:

CHO-K1 cells stably expressing CXCR2 and Gα16 were grown to 80% confluency in DMEM/F12 (HAM's) 1:1, w/10% FCS (heat inactivated), w/2 mM L-glutamine, w/0.4 mg/ml G418 while maintained at 37° C. in a 5% $CO_2$ incubator. Twenty four hours previous to assay, cells were harvested and plated, 40,000 cells per well, in a 96 well, black wall, clear bottom plate (Packard View) and returned to $CO_2$ incubator. On the day of assay, compounds were serially diluted in 100% DMSO to 300× the desired assay concentration. Growth media is aspirated off cells and replaced with 100 ul of load media (EMEM with Earl's salts w/L-Glutamine, 0.1% BSA, (Bovuminar Cohen Fraction V from Seriologicals Corp.), 4 uM Fluo-4-acetoxymethyl ester fluorescent indicator dye (Fluo-4 AM, from Molecular Probes), and 2.5 mM probenecid) and incubated for 1 hour at 37° C. in $CO_2$ incubator. Load media was aspirated and replaced with 100 uL of EMEM with Earl's salts w/L-Glutamine, 0.1% gelatin, and 2.5 mM probenecid and incubated for an additional 10 min. Serially diluted compound (3 ul) in DMSO at 300× was transferred to a 96 well plate containing 297 micro liters of KRH (120 mM NaCl, 4.6 mM KCl, 1.03 mM $KH_2PO_4$, 25 mM $NaHCO_3$, 1.0 mM $CaCl_2$, 1.1 mM $MgCl_2$, 11 mM Glucose, 20 mM HEPES (pH 7.4)) w/2.5 mM probenecid and 0.1% gelatin (compound now at 3×). Media was aspirated off cells, and cells washed 3 times with KRH w/2.5 mM probenecid, w/0.1% gelatin. KRH (100 ul) w/2.5 mM probenecid with 0.1% gelatin was added to wells then 50 ul of 3× compound in KRH w/2.5 mM probenecid and 0.1% gelatin was added to wells (compound now at IX) and incubated at 37° C. in $CO_2$ incubator for 10 min. Plates were placed onto FLIPR (Fluorometric Imaging Plate Reader, Molecular Devices, Sunnyvale Calif.) for analysis as described previously (Sarau et al., 1999). The percent of maximal human IL-8 induced $Ca^{2+}$ mobilization induced by 1.0 nM IL-8, an $EC_{80}$ conc. for CXCR2, was determined for each concentration of compound and the $IC_{50}$ calculated as the concentration of test compound that inhibits 50% of the maximal response induced by 1.0 nM IL-8. Examples 1-53 exhibited positive inhibitory activity in this assay at $IC_{50}$ values of <10 uM, and would be considered active. Compounds tested by the above assay had an $IC_{50}$ from about 900 nM to about 13 nM.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A compound according to Formula (I):

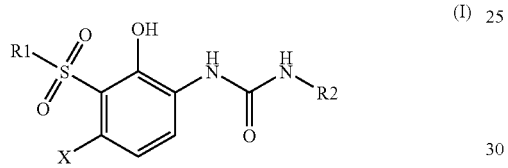

wherein

X is selected from the group consisting of halogen, $C_{1-3}$alkyl, $C_{1-3}$alkoxy, cyano, $CF_3$, and $OCF_3$;

R2 is selected from the group consisting of $C_{3-6}$cycloalkyl, phenyl and heteroaryl, wherein the phenyl or heteroaryl moieties are optionally substituted, once or twice, independently, by a substituent selected from the group consisting of $C_{1-3}$alkyl, halogen, $CF_3$, $OCF_3$, phenyloxy and benzyloxy; or R2 represents phenyl substituted by methylenedioxy or (di-halo-substituted)-methylenedioxy;

R1 is

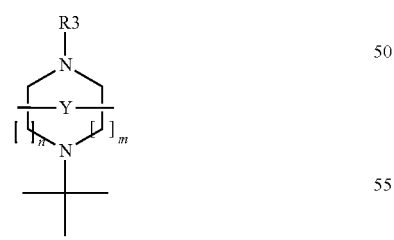  a)

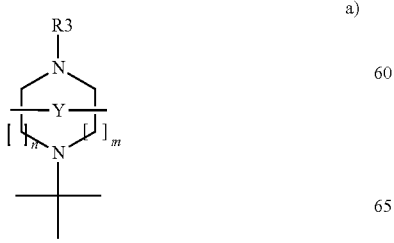

-continued

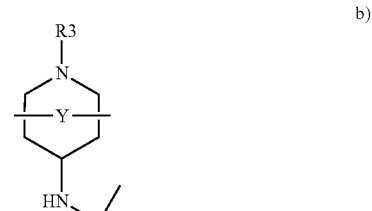  b)

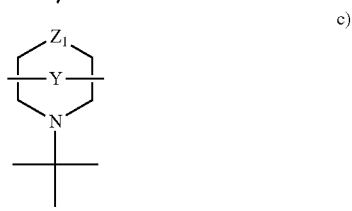  c)

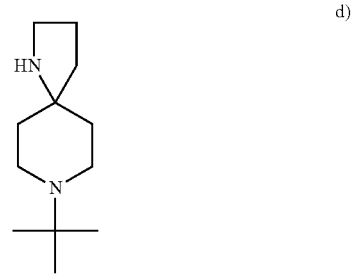  d)

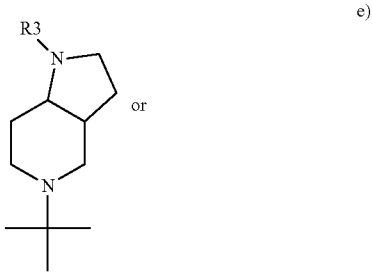  e)

or

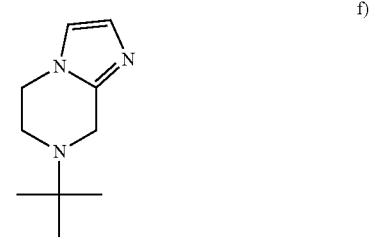  f)

R3 is selected, independently, at each occurrence, from the group consisting of hydrogen, $C_{1-6}$alkyl, $C_{1-6}$alkoxy, $C_{3-7}$cycloalkyl, $C_{3-7}$cycloalkyl $C_{1-3}$-alkyl, phenyl and phenyl$C_{1-3}$-alkyl, wherein the alkyl, cycloalkyl or phenyl moieties are optionally substituted, once or twice, independently, by a substituent selected from the group consisting of $C_{1-3}$alkyl, halogen, OH, $CF_3$, and $OCF_3$;

Y is a $C_{1-4}$-alkyl diradical attached to the ring system in two positions;

m is 1; and n is 1;

or a pharmaceutically acceptable salt thereof.

2. A compound according to claim 1 wherein X is halogen.

3. A compound according to claim 2 wherein X is chlorine.

4. A compound according to claim 1 wherein R2 is phenyl, optionally substituted, independently, once or twice, by a substituent selected from the group consisting of $C_{1-3}$alkyl, halogen, $OCF_3$ and phenyloxy.

5. A compound according to claim 1 wherein R2 is selected from the group consisting of 3-fluoro-2-methylphenyl, 2-trifluoromethyloxyphenyl, 2-chloro-3-fluorophenyl, 2-ethylphenyl or 2-phenoxyphenyl.

6. A compound according to claim 5 wherein R2 is 3-fluoro-2-methylphenyl, or 2-chloro-3-fluorophenyl.

7. A pharmaceutical composition comprising a compound according to claim 1 and a pharmaceutically acceptable carrier or diluent.

8. A method of synthesizing a compound according to claim 1 comprising the steps of:

a) hydrolyzing a benzoxazole according to formula (II):

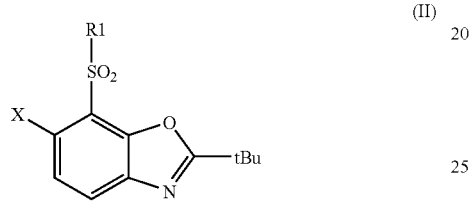
(II)

wherein R1 is as defined according to claim 1;
to form an aminophenol according to formula (III):

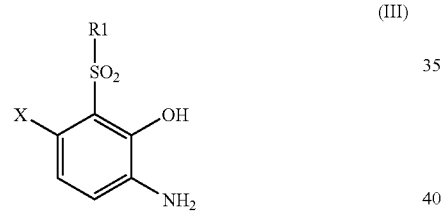
(III)

and b) exposing the aminophenol to an isocyanate or isocyanate precursor of the formula R2C=N=O or R2CON3 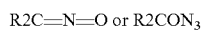

wherein R2 is as defined according to claim 1;
to form a final product according to formula (IV):

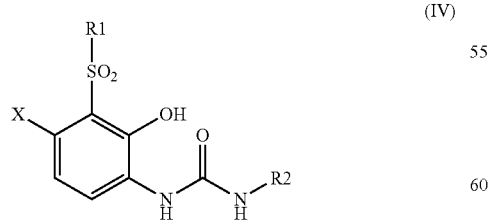
(IV)

wherein X, R1 and R2 are as defined according to claim 1; and wherein the R1 moiety is protected by an acid labile protecting group which is subsequently removed as necessary.

9. An intermediate according to formula (II) or (III):

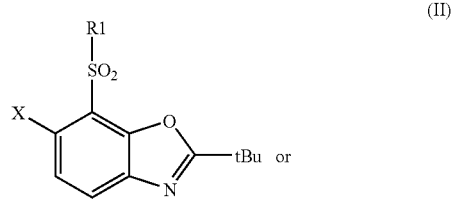
(II)

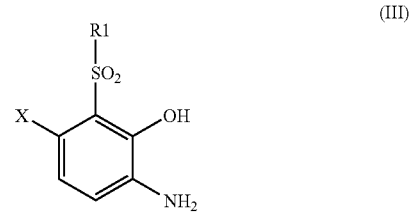
(III)

wherein
R1 is

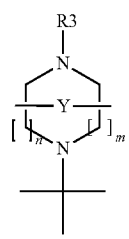
a)

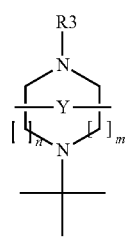
b)

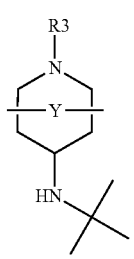

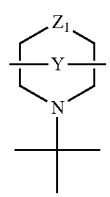
c)

d)

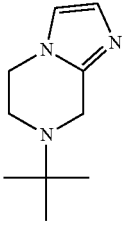

e)

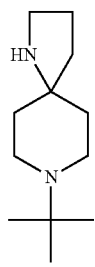

or

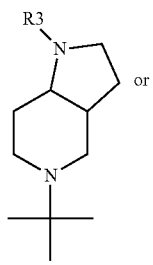

f)

R3 is selected, independently, at each occurrence, from the group consisting of hydrogen, $C_{1-6}$alkyl, $C_{1-6}$alkoxy, $C_{3-7}$cycloalkyl, $C_{3-7}$cycloalkyl $C_{1-3}$-alkyl, phenyl and phenyl$C_{1-3}$alkyl, wherein the alkyl, cycloalkyl or phenyl moieties are optionally substituted, once or twice, independently, by a substituent selected from the group consisting of $C_{1-3}$alkyl, halogen, OH, $CF_3$, and $OCF_3$;

Y is a $C_{1-4}$-alkyl diradical attached to the ring system in two positions; and X is selected from the group consisting of halogen, $C_{1-3}$alkyl, $C_{1-3}$alkoxy, cyano, $CF_3$, and $OCF_3$.

* * * * *